(12) United States Patent
Ainsworth et al.

(10) Patent No.: US 8,167,947 B2
(45) Date of Patent: May 1, 2012

(54) METHODS FOR PUSH DISTRACTION AND FOR PROVISION OF THERAPY TO ADJACENT MOTION SEGMENTS

(75) Inventors: Stephen D. Ainsworth, Wilmington, NC (US); Robert L. Assell, St. Paul, MN (US); Andrew H. Cragg, Edina, MN (US); Bradley Wessman, Wilmington, NC (US)

(73) Assignee: TranS1 Inc., Wilmington, NC (US)

( * ) Notice: Subject to any disclaimer, the term of this patent is extended or adjusted under 35 U.S.C. 154(b) by 177 days.

(21) Appl. No.: 12/821,286

(22) Filed: Jun. 23, 2010

(65) Prior Publication Data

US 2011/0035005 A1 Feb. 10, 2011

Related U.S. Application Data

(60) Division of application No. 11/202,655, filed on Aug. 13, 2005, now Pat. No. 7,776,042, which is a continuation-in-part of application No. 12/339,932, filed on Dec. 19, 2008, now abandoned, which is a continuation of application No. 10/972,039, filed on Oct. 22, 2004, now Pat. No. 7,491,236, said application No. 11/202,655 is a continuation-in-part of application No. 11/189,943, filed on Jul. 26, 2005, now Pat. No. 7,608,077, which is a continuation of application No. 10/309,416, filed on Dec. 3, 2002, now Pat. No. 6,921,403.

(60) Provisional application No. 60/601,842, filed on Aug. 14, 2004, provisional application No. 60/513,899, filed on Oct. 23, 2003.

(51) Int. Cl.
*A61F 2/44* (2006.01)

(52) U.S. Cl. .................................................. 623/17.11
(58) Field of Classification Search .... 623/17.11–17.16; 606/279, 246, 86 A, 191, 256
See application file for complete search history.

(56) References Cited

U.S. PATENT DOCUMENTS

| 1,442,051 A | 1/1923 | Cummings |
| 2,336,338 A | 12/1943 | Zublin ........................ 255/1.6 |

(Continued)

FOREIGN PATENT DOCUMENTS

WO    WO 91/00713    1/1991

(Continued)

OTHER PUBLICATIONS

International Search Report and Written Opinion From PCT Application Corresponding to Parent Case, Application No. PCT/US2005/028847, Nov. 13, 2006 (11 pgs).

(Continued)

*Primary Examiner* — Pedro Philogene
(74) *Attorney, Agent, or Firm* — Kevin E. Flynn; Flynn IP Law

(57) ABSTRACT

Disclosed are methods and apparatus for the provision of spinal therapy to two or more adjacent motion segments accessed through a trans-sacral approach. The spinal therapies include fusion and dynamic stabilization with and without a distraction of the most cephalad motion segment of the two or more adjacent motion segments provided therapy. The disclosure includes methods and apparatus to impart a push distraction to increase the distance between two adjacent vertebrae. Related concepts for the extraction of previously inserted devices and the delivery and removal of plugs for plugging the interior cavities of implantable devices are disclosed.

27 Claims, 17 Drawing Sheets

U.S. PATENT DOCUMENTS

| | | | | |
|---|---|---|---|---|
| 2,586,556 A | 2/1952 | Mullikin | | 85/1 |
| 3,367,326 A | 2/1968 | Frazier | | 128/92 |
| 3,454,006 A | 7/1969 | Langdon | | 128/214.4 |
| 3,598,108 A | 8/1971 | Jamshidi et al. | | 128/2 B |
| 3,620,216 A | 11/1971 | Szymanski | | 128/217 |
| 3,628,524 A | 12/1971 | Jamshidi | | 128/2 B |
| 3,788,320 A | 1/1974 | Dye | | 128/221 |
| 3,837,347 A | 9/1974 | Tower | | 128/404 |
| 3,892,232 A | 7/1975 | Neufeld | | 128/92 EB |
| 3,893,445 A | 7/1975 | Hofsess | | 128/2 B |
| 3,993,079 A | 11/1976 | Gatztañondo | | 128/347 |
| 4,046,144 A | 9/1977 | McFarlane | | 128/214.4 |
| 4,175,555 A | 11/1979 | Herbert | | 128/92 B |
| 4,202,332 A | 5/1980 | Tersteegen et al. | | 128/214.4 |
| 4,266,555 A | 5/1981 | Jamshidi | | 128/753 |
| 4,276,874 A | 7/1981 | Wolvek et al. | | 128/1 D |
| 4,309,777 A | 1/1982 | Patil | | 3/1.91 |
| 4,513,754 A | 4/1985 | Lee | | 128/753 |
| 4,518,383 A | 5/1985 | Evans | | 604/51 |
| 4,553,273 A | 11/1985 | Wu | | 623/18 |
| 4,554,914 A | 11/1985 | Kapp et al. | | 128/92 C |
| 4,573,448 A | 3/1986 | Kambin | | 128/1 R |
| 4,607,632 A | 8/1986 | Brennan et al. | | 128/743 |
| 4,609,370 A | 9/1986 | Morrison | | 604/165 |
| 4,636,217 A | 1/1987 | Ogilvie et al. | | 623/17 |
| 4,650,466 A | 3/1987 | Luther | | 604/95 |
| 4,654,030 A | 3/1987 | Moll et al. | | 604/165 |
| 4,657,550 A | 4/1987 | Daher | | 623/17 |
| 4,721,506 A | 1/1988 | Teves | | 604/51 |
| 4,772,266 A | 9/1988 | Groshong | | 604/164 |
| 4,790,303 A | 12/1988 | Steffee | | 128/924 M |
| 4,808,155 A | 2/1989 | Mahurkar | | 604/43 |
| 4,854,797 A | 8/1989 | Gourd | | 411/383 |
| 4,858,601 A | 8/1989 | Glisson | | 128/92 R |
| 4,862,891 A | 9/1989 | Smith | | 128/343 |
| 4,873,978 A | 10/1989 | Ginsburg | | 128/345 |
| 4,922,602 A | 5/1990 | Mehl | | 29/460 |
| 4,969,887 A | 11/1990 | Sodhi | | 606/67 |
| 4,969,888 A | 11/1990 | Scholten et al. | | 606/94 |
| 4,994,036 A | 2/1991 | Biscoping et al. | | 604/164 |
| 5,002,546 A | 3/1991 | Romano | | 606/80 |
| 5,002,576 A | 3/1991 | Fuhrmann et al. | | 623/17 |
| 5,009,659 A | 4/1991 | Hamlin et al. | | 606/159 |
| 5,019,080 A * | 5/1991 | Hemer | | 606/104 |
| 5,059,193 A | 10/1991 | Kuslich | | 606/61 |
| 5,061,137 A | 10/1991 | Gourd | | 411/510 |
| 5,090,419 A | 2/1992 | Palestrant | | 128/754 |
| 5,102,276 A | 4/1992 | Gourd | | 411/392 |
| 5,108,430 A | 4/1992 | Ravo | | 623/12 |
| 5,147,404 A | 9/1992 | Downey | | 623/17 |
| 5,169,387 A | 12/1992 | Kronner | | 604/51 |
| 5,231,910 A | 8/1993 | Harsch et al. | | 83/875 |
| 5,246,458 A | 9/1993 | Graham | | 623/17 |
| 5,261,888 A | 11/1993 | Semm | | 604/164 |
| 5,279,553 A | 1/1994 | Winkler et al. | | 604/53 |
| 5,290,247 A | 3/1994 | Crittenden | | 604/171 |
| 5,295,974 A | 3/1994 | O'Laughlin | | 604/198 |
| 5,336,223 A | 8/1994 | Rogers | | 606/61 |
| 5,338,297 A | 8/1994 | Kocur et al. | | 604/96 |
| 5,344,315 A | 9/1994 | Hanson | | 433/20 |
| 5,370,653 A | 12/1994 | Cragg | | 606/170 |
| 5,376,094 A | 12/1994 | Kline | | 606/113 |
| 5,380,292 A | 1/1995 | Wilson | | 604/164 |
| 5,385,561 A | 1/1995 | Cerny | | 604/264 |
| 5,427,115 A | 6/1995 | Rowland et al. | | 128/756 |
| 5,431,676 A | 7/1995 | Dubrul et al. | | 606/185 |
| 5,445,140 A | 8/1995 | Tovey | | 600/117 |
| 5,445,619 A | 8/1995 | Burns | | 604/192 |
| 5,476,467 A | 12/1995 | Benoist | | 606/100 |
| 5,478,328 A | 12/1995 | Silverman et al. | | 604/272 |
| 5,490,859 A | 2/1996 | Mische et al. | | 606/159 |
| 5,515,871 A | 5/1996 | Bittner et al. | | 128/898 |
| 5,535,756 A | 7/1996 | Parasher | | 128/756 |
| 5,571,133 A | 11/1996 | Yoon | | 606/185 |
| 5,571,192 A | 11/1996 | Schönhöffer | | 623/17 |
| 5,591,170 A | 1/1997 | Spievack et al. | | 606/82 |
| 5,669,882 A | 9/1997 | Pyles | | 604/164 |
| 5,685,852 A | 11/1997 | Turkel et al. | | 604/159 |
| 5,685,857 A | 11/1997 | Negus et al. | | 604/170 |
| 5,685,877 A | 11/1997 | Pagedas et al. | | 606/46 |
| 5,702,453 A | 12/1997 | Rabbe et al. | | 623/17 |
| 5,702,455 A | 12/1997 | Saggar | | 623/17 |
| 5,718,237 A | 2/1998 | Haaga | | 128/751 |
| 5,722,423 A | 3/1998 | Lind et al. | | 128/756 |
| 5,733,284 A | 3/1998 | Martin | | 606/61 |
| 5,735,813 A | 4/1998 | Lewis | | 604/43 |
| 5,743,912 A | 4/1998 | Labille et al. | | 606/65 |
| 5,807,277 A | 9/1998 | Swaim | | 600/567 |
| 5,807,318 A | 9/1998 | St. Goar et al. | | 604/53 |
| 5,810,788 A | 9/1998 | Racz | | 604/272 |
| 5,827,285 A * | 10/1998 | Bramlet | | 606/60 |
| 5,843,048 A | 12/1998 | Gross | | 604/264 |
| 5,882,329 A | 3/1999 | Patterson et al. | | 604/49 |
| 5,902,279 A | 5/1999 | Powles et al. | | 604/239 |
| 5,916,208 A | 6/1999 | Luther et al. | | 604/508 |
| 5,916,267 A | 6/1999 | Tienboon | | 623/17 |
| 5,919,172 A | 7/1999 | Golba, Jr. | | 604/272 |
| 5,921,971 A | 7/1999 | Agro et al. | | 604/280 |
| 5,928,239 A | 7/1999 | Mirza | | 606/79 |
| 5,935,131 A | 8/1999 | Bonutti | | 606/80 |
| 5,937,524 A | 8/1999 | Hornsby | | 30/113.1 |
| 5,954,671 A | 9/1999 | O'Neill | | 600/567 |
| 5,972,015 A | 10/1999 | Scribner et al. | | 606/192 |
| 5,979,056 A | 11/1999 | Andrews | | 30/49 |
| 5,989,290 A | 11/1999 | Biedermann et al. | | 623/17 |
| 6,010,495 A | 1/2000 | Tilton, Jr. | | 606/1 |
| 6,036,658 A | 3/2000 | Leet et al. | | 600/569 |
| 6,036,696 A | 3/2000 | Lambrecht et al. | | 606/97 |
| 6,053,916 A * | 4/2000 | Moore | | 623/16.11 |
| 6,056,749 A | 5/2000 | Kuslich | | 606/61 |
| 6,086,589 A * | 7/2000 | Kuslich et al. | | 606/247 |
| 6,093,196 A | 7/2000 | Okada | | 606/127 |
| 6,093,205 A | 7/2000 | McLeod et al. | | 623/17 |
| RE36,857 E | 9/2000 | Euteneuer et al. | | 604/102 |
| 6,113,614 A | 9/2000 | Mears | | 606/159 |
| 6,127,597 A | 10/2000 | Beyar et al. | | 623/16 |
| 6,159,179 A | 12/2000 | Simonson | | 604/117 |
| 6,159,212 A | 12/2000 | Schoedinger, III et al. | | 606/61 |
| 6,187,000 B1 | 2/2001 | Davison et al. | | 606/1 |
| 6,217,509 B1 | 4/2001 | Foley et al. | | 600/114 |
| 6,235,043 B1 | 5/2001 | Reiley et al. | | 606/192 |
| 6,241,734 B1 | 6/2001 | Scribner et al. | | 606/93 |
| 6,258,044 B1 | 7/2001 | Lonky et al. | | 600/569 |
| 6,280,191 B1 | 8/2001 | Gordon | | 433/173 |
| 6,306,132 B1 | 10/2001 | Moorman et al. | | 606/41 |
| 6,306,143 B1 | 10/2001 | Kvarnstrom et al. | | 606/105 |
| 6,306,163 B1 | 10/2001 | Fitz | | 623/1.12 |
| 6,319,242 B1 | 11/2001 | Patterson et al. | | 604/508 |
| 6,319,254 B1 | 11/2001 | Giet et al. | | 606/73 |
| 6,371,968 B1 | 4/2002 | Kogasaka et al. | | 606/190 |
| 6,383,188 B2 | 5/2002 | Kuslich et al. | | 606/80 |
| 6,383,190 B1 | 5/2002 | Preissman | | 606/94 |
| 6,395,034 B1 | 5/2002 | Suddaby | | 623/17.15 |
| 6,398,758 B1 | 6/2002 | Jacobsen et al. | | 604/104 |
| 6,402,750 B1 | 6/2002 | Atkinson et al. | | 606/61 |
| 6,416,484 B1 | 7/2002 | Miller et al. | | 600/564 |
| 6,419,639 B2 | 7/2002 | Walther et al. | | 600/562 |
| RE37,815 E | 8/2002 | Rizvi | | 606/222 |
| 6,440,138 B1 | 8/2002 | Reiley et al. | | 606/79 |
| 6,485,518 B1 | 11/2002 | Cornwall et al. | | 623/17.11 |
| 6,506,194 B1 | 1/2003 | Hajianpour | | 606/95 |
| 6,517,543 B1 * | 2/2003 | Berrevoets et al. | | 606/304 |
| 6,520,953 B1 | 2/2003 | Schultz | | 606/1 |
| 6,558,353 B2 | 5/2003 | Zohmann | | 604/158 |
| 6,558,386 B1 | 5/2003 | Cragg | | 606/61 |
| 6,558,390 B2 | 5/2003 | Cragg | | 606/80 |
| 6,572,593 B1 | 6/2003 | Daum | | 604/264 |
| 6,575,979 B1 | 6/2003 | Cragg | | 606/86 |
| 6,582,441 B1 | 6/2003 | He et al. | | 606/129 |
| 6,582,466 B1 | 6/2003 | Gauchet | | 623/17.11 |
| 6,582,468 B1 | 6/2003 | Gauchet | | 623/17.16 |
| 6,607,530 B1 | 8/2003 | Carl et al. | | 606/61 |
| 6,610,091 B1 | 8/2003 | Reiley | | 623/17.11 |
| 6,626,903 B2 | 9/2003 | McGuckin, Jr. et al. | | 606/45 |
| 6,626,943 B2 | 9/2003 | Eberlein et al. | | 623/17.15 |
| 6,645,248 B2 | 11/2003 | Casutt | | 623/17.12 |
| 6,652,535 B2 | 11/2003 | Kvarnstrom et al. | | 606/105 |

| | | | | | | | |
|---|---|---|---|---|---|---|---|
| 6,656,184 | B1 | 12/2003 | White et al. ............... 606/73 | 2001/0047169 | A1 | 11/2001 | McGuckin, Jr. et al. ....... 606/45 |
| 6,669,699 | B1 | 12/2003 | Ralph et al. ............... 606/61 | 2002/0035400 | A1 | 3/2002 | Bryan et al. ............... 623/17.15 |
| 6,682,561 | B2 | 1/2004 | Songer et al. ............ 623/17.11 | 2002/0068975 | A1 | 6/2002 | Teitelbaum et al. ........ 623/17.11 |
| 6,692,495 | B1 | 2/2004 | Zacouto ............... 606/61 | 2002/0099384 | A1 | 7/2002 | Scribner et al. ............... 606/92 |
| 6,726,681 | B2 | 4/2004 | Grasso, III et al. ........... 606/15 | 2002/0188299 | A1 | 12/2002 | Reiley et al. ............... 606/79 |
| 6,730,088 | B2 | 5/2004 | Yeh ............... 606/61 | 2002/0198527 | A1 | 12/2002 | Muckter ............... 606/73 |
| 6,733,532 | B1 | 5/2004 | Gauchet et al. ........... 623/17.12 | 2003/0028193 | A1 | 2/2003 | Weil et al. ............... 606/73 |
| 6,733,533 | B1 | 5/2004 | Lozier ............... 623/17.12 | 2003/0078465 | A1 | 4/2003 | Pai et al. ............... 600/16 |
| 6,740,090 | B1 | 5/2004 | Cragg et al. ............... 606/79 | 2003/0083668 | A1 | 5/2003 | Rogers et al. ............... 606/100 |
| 6,746,451 | B2 | 6/2004 | Middleton et al. ........... 606/79 | 2003/0083688 | A1 | 5/2003 | Simonson ............... 606/191 |
| 6,749,595 | B1 | 6/2004 | Murphy ............... 604/500 | 2003/0114930 | A1 | 6/2003 | Lim et al. ............... 623/17.11 |
| 6,764,489 | B2 | 7/2004 | Ferree ............... 606/61 | 2003/0130577 | A1 | 7/2003 | Purdy et al. ............... 600/433 |
| 6,770,070 | B1 | 8/2004 | Balbierz ............... 606/41 | 2003/0181982 | A1 | 9/2003 | Kuslich ............... 623/17.16 |
| 6,790,210 | B1 | 9/2004 | Cragg et al. ............... 606/80 | 2003/0191474 | A1 | 10/2003 | Cragg et al. ............... 606/79 |
| 6,805,697 | B1 | 10/2004 | Helm et al. ............... 606/92 | 2003/0195518 | A1 | 10/2003 | Cragg et al. ............... 606/80 |
| 6,821,276 | B2 | 11/2004 | Lambrecht et al. ........... 606/45 | 2003/0204189 | A1 | 10/2003 | Cragg ............... 606/61 |
| 6,821,277 | B2 | 11/2004 | Teitelbaum ............... 606/61 | 2003/0212400 | A1 | 11/2003 | Bloemer et al. ............... 606/61 |
| 6,896,202 | B1 | 5/2005 | Fugere ............... 239/291 | 2004/0083002 | A1 | 4/2004 | Belef et al. ............... 623/17.16 |
| 6,899,716 | B2 | 5/2005 | Cragg ............... 606/86 | 2004/0087942 | A1 | 5/2004 | McGuckin, Jr. et al. ....... 606/45 |
| 6,921,403 | B2 | 7/2005 | Cragg et al. ............... 606/86 | 2004/0106940 | A1 | 6/2004 | Shaolian et al. ............... 606/170 |
| 6,936,211 | B2 | 8/2005 | Binner et al. ............... 264/295 | 2004/0215343 | A1 | 10/2004 | Hochschuler et al. ..... 623/17.12 |
| 6,964,665 | B2 | 11/2005 | Thomas et al. ............... 606/61 | 2004/0230309 | A1 | 11/2004 | DiMauro et al. ........... 623/17.12 |
| 6,966,921 | B2 | 11/2005 | Scheller et al. ............... 606/166 | 2005/0043796 | A1 | 2/2005 | Grant et al. ............... 623/17.11 |
| 7,011,647 | B2 | 3/2006 | Purdy et al. ............... 604/164.04 | 2005/0113919 | A1 | 5/2005 | Cragg et al. ............... 623/17.11 |
| 7,014,633 | B2 | 3/2006 | Cragg ............... 604/500 | 2005/0113929 | A1 | 5/2005 | Cragg et al. ............... 623/17.16 |
| 7,025,746 | B2 | 4/2006 | Tal ............... 604/164.1 | 2005/0137601 | A1 | 6/2005 | Assell et al. ............... 606/79 |
| 7,048,717 | B1 | 5/2006 | Frassica ............... 604/165.04 | 2005/0137604 | A1 | 6/2005 | Assell et al. ............... 606/93 |
| 7,052,500 | B2 | 5/2006 | Bashiri et al. ............... 606/113 | 2005/0137605 | A1 | 6/2005 | Assell et al. ............... 606/96 |
| 7,063,703 | B2 | 6/2006 | Reo ............... 606/79 | 2005/0137607 | A1 | 6/2005 | Assell et al. ............... 606/100 |
| 7,081,123 | B2 | 7/2006 | Merboth et al. ............... 606/185 | 2005/0149049 | A1 | 7/2005 | Assell et al. ............... 606/99 |
| 7,087,056 | B2 | 8/2006 | Vaughan ............... 606/61 | 2005/0177117 | A1 | 8/2005 | Crocker et al. ............... 604/272 |
| 7,087,058 | B2 | 8/2006 | Cragg ............... 606/86 | 2005/0177167 | A1 | 8/2005 | Muckter ............... 606/73 |
| 7,128,760 | B2 | 10/2006 | Michelson ............... 623/17.15 | 2005/0277940 | A1 | 12/2005 | Neff ............... 606/73 |
| 7,156,877 | B1 | 1/2007 | Lotz et al. ............... 623/17.16 | 2006/0085073 | A1 | 4/2006 | Raiszadeh ............... 623/17.12 |
| 7,291,150 | B2 | 11/2007 | Graf ............... 606/61 | 2007/0093847 | A1 | 4/2007 | Scribner et al. ............... 606/93 |
| 7,309,338 | B2 | 12/2007 | Cragg ............... 606/80 | 2007/0106383 | A1 | 5/2007 | Abdou ............... 623/17.11 |
| 7,329,259 | B2 | 2/2008 | Cragg ............... 606/61 | 2008/0195156 | A1 | 8/2008 | Ainsworth et al. ........... 606/279 |
| 7,473,256 | B2 | 1/2009 | Assell et al. ............... 606/90 | 2009/0105768 | A1 | 4/2009 | Cragg et al. ............... 606/301 |
| 7,491,236 | B2 | 2/2009 | Cragg et al. ............... 623/17.11 | 2009/0131734 | A1 | 5/2009 | Neustadter et al. ............... 600/8 |
| 7,500,977 | B2 | 3/2009 | Assell et al. ............... 606/79 | | | | |
| 7,530,993 | B2 | 5/2009 | Assell et al. ............... 606/279 | | | | |
| 7,547,324 | B2 * | 6/2009 | Cragg et al. ............... 623/17.11 | | | | |
| 7,569,056 | B2 | 8/2009 | Cragg et al. ............... 606/79 | | | | |
| 7,588,574 | B2 | 9/2009 | Assell et al. ............... 606/86 R | | | | |
| 7,608,077 | B2 | 10/2009 | Cragg et al. ............... 606/86 R | | | | |
| 7,662,173 | B2 | 2/2010 | Cragg et al. ............... 606/279 | | | | |
| 7,717,958 | B2 | 5/2010 | Cragg et al. ............... 623/17.12 | | | | |
| 7,740,633 | B2 | 6/2010 | Assell et al. ............... 606/96 | | | | |
| 7,776,042 | B2 * | 8/2010 | Ainsworth et al. ......... 606/86 A | | | | |
| 7,776,068 | B2 * | 8/2010 | Ainsworth et al. ........... 606/246 | | | | |
| 2001/0021852 | A1 | 9/2001 | Chappius ............... 606/73 | | | | |
| 2001/0034495 | A1 | 10/2001 | Wilson et al. ............... 600/564 | | | | |
| 2001/0034525 | A1 | 10/2001 | Staehlin et al. ............... 606/79 | | | | |

FOREIGN PATENT DOCUMENTS

WO      WO 01/60234 A2      8/2001

OTHER PUBLICATIONS

Office Action from U.S. Appl. No. 11/202,655 dated Nov. 16, 2009 (9 pgs).

International Search Report and Written Opinion From Related PCT Application, Application No. PCT/US2010/045135, Oct. 6, 2010 (15 pgs).

* cited by examiner

FIG. 5
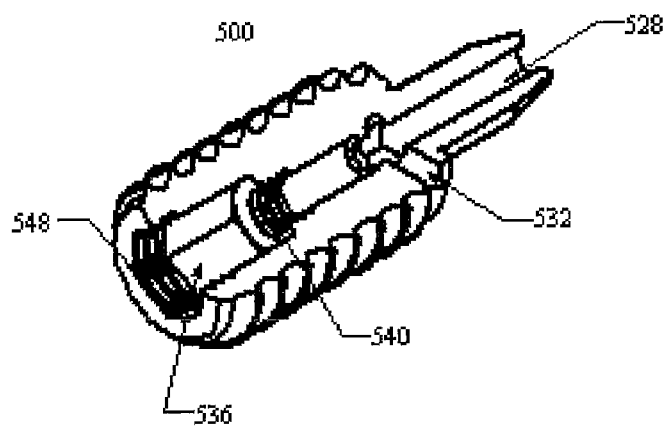
FIG. 5C
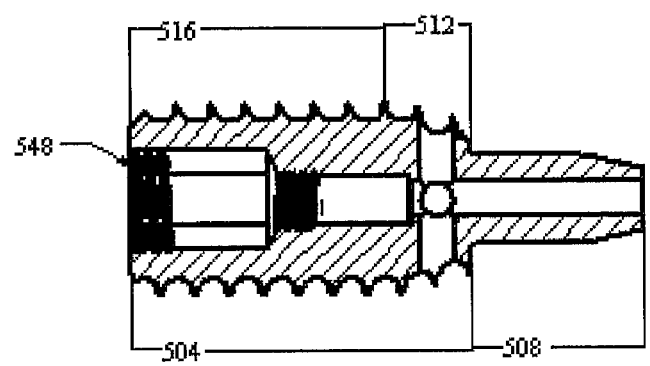
FIG. 5B
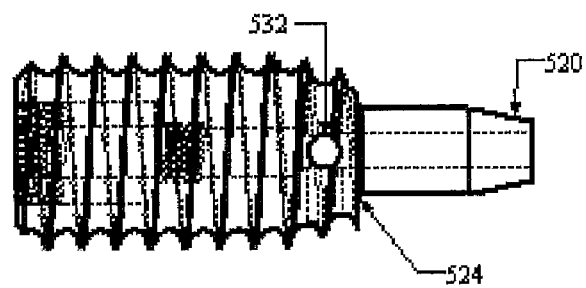
FIG. 5A

FIG. 8
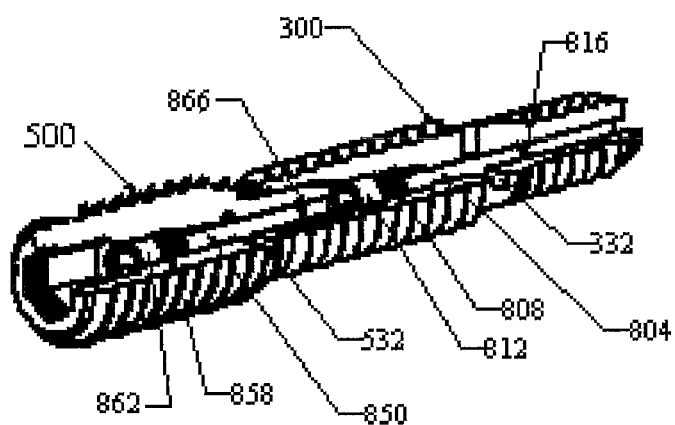
FIG. 8B
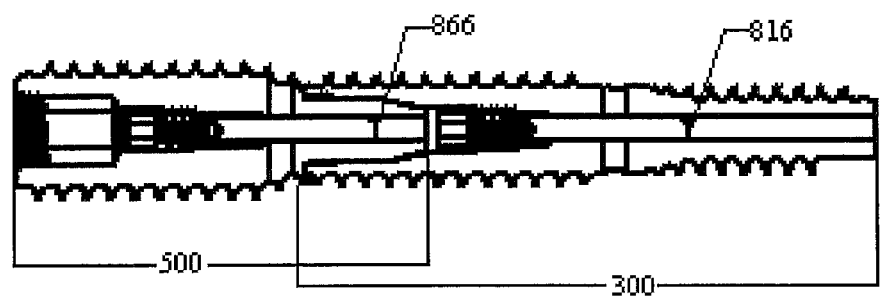
FIG. 8A

FIG. 9

| |
|---|
| 905 Prepare Channel |
| ↓ |
| 910 Engage Distal Distraction Rod with Both Vertebral Bodies |
| ↓ |
| 915 Rotate to Obtain Desired Distraction of Distal Intervertebral Space |
| ↓ |
| 920 Apply Therapy to Distracted Distal Intervertebral Space |
| ↓ |
| 925 Add Distal Distraction Rod Bore Plug (if desired) |
| ↓ |
| 930 Engage Proximal Distraction Rod with Proximal Vertebral Body |
| ↓ |
| 935 Rotate Proximal Distraction Rod to Push Against Distal Distraction Rod to Impose Desired Distraction of Proximal Intervertebral Space |
| ↓ |
| 940 Apply Therapy to Proximal Intervertebral Space |

| ↓ | ↓ | ↓ |
|---|---|---|
| 945 Add Proximal Distraction Rod Bore Plug within Proximal Distraction Rod | 950 Engage Proximal Distraction Rod Bore Plug with Distal Distraction Rod | 955 Engage Proximal Distraction Rod Bore Plug with Distal Distraction Rod Bore Plug |

FIG. 14
FIG. 14A
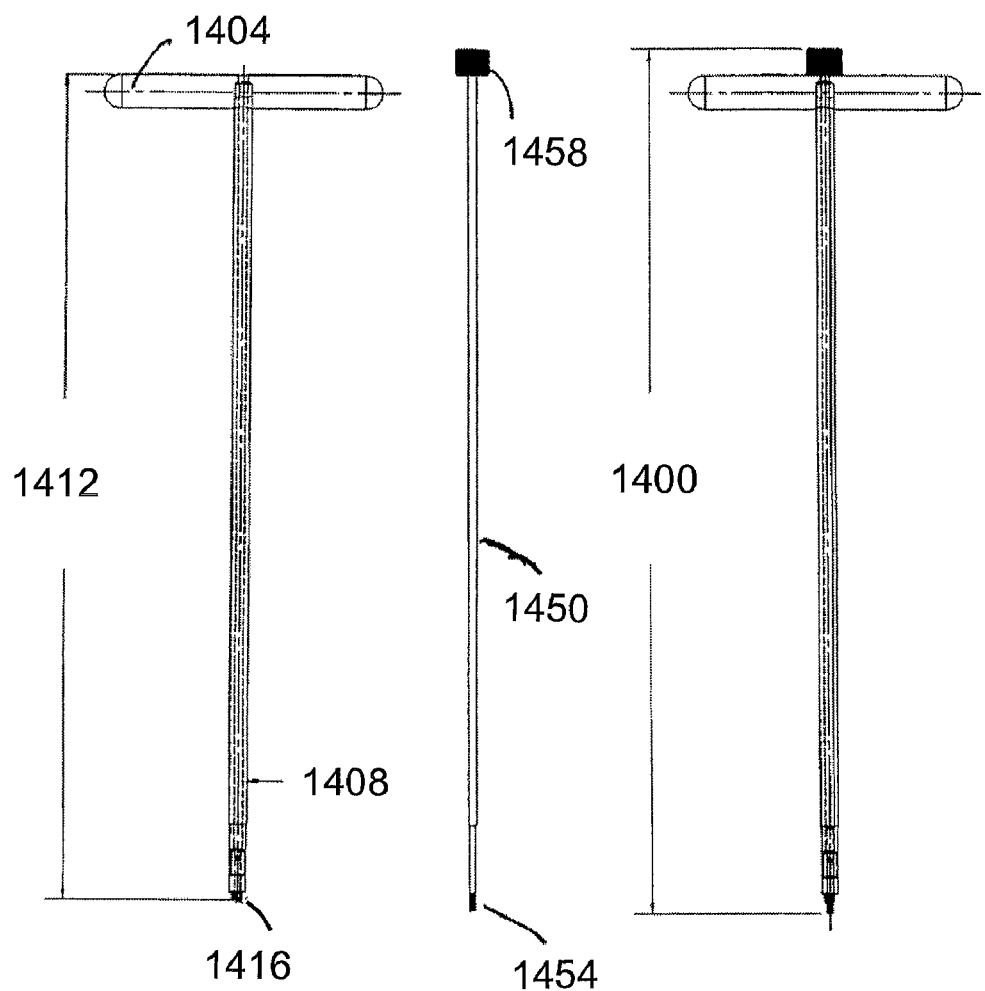
FIG. 14B
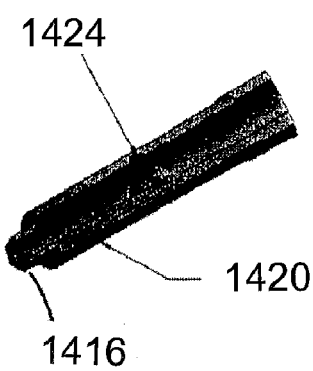
FIG. 14C
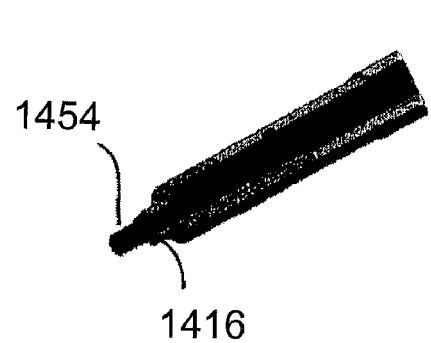

METHODS FOR PUSH DISTRACTION AND FOR PROVISION OF THERAPY TO ADJACENT MOTION SEGMENTS

This application claims priority and incorporates by reference and commonly assigned U.S. patent application Ser. No. 11/202,655 filed Aug. 13, 2005 for Methods and Apparatus for Provision of Therapy to Adjacent Motion Segments. Through the '655 application, this application claims priority and incorporates by reference U.S. Provisional Application No. 60/601,842 filed Aug. 14, 2004 for Method & Apparatus for Multi-Level Stabilization of the Spine and U.S. patent application Ser. No. 11/189,943, now U.S. Pat. No. 7,608,077 for Method And Apparatus for Spinal Distraction and Fusion.

This application claims priority and incorporated by reference and commonly assigned U.S. patent application Ser. No. 12/339,932 for Dual Anchor Prosthetic Nucleus Apparatus which is a continuation of U.S. patent application Ser. No. 10/972,039 now U.S. Pat. No. 7,491,236 for Dual Anchor Prosthetic Nucleus Apparatus. U.S. patent application Ser. No. 10/972,039 filed Oct. 22, 2004 claims priority and benefits from and commonly assigned U.S. Provisional Patent Application No. 60/513,899 filed Oct. 23, 2003 for Surgical Instrumentation and Implants for Spinal Procedures. The present application claims priority to and incorporates by reference application Ser. Nos. 10/972,039 and 60/513,899.

This application extends the work done by TranS1 Inc. and incorporates by reference a set of Unites States applications, provisional applications, and issued patents including: Ser. No. 11/189,943 filed Jul. 26, 2005 (now issued as U.S. Pat. No. 7,608,077); Ser. No. 10/309,416 filed Dec. 3, 2002 (now issued as U.S. Pat. No. 6,921,403); 60/182,748 filed Feb. 16, 2000; Ser. No. 09/640,222 filed Aug. 16, 2000 (now issued as U.S. Pat. No. 6,575,979); Ser. No. 10/459,149 filed Jun. 11, 2003 (now issued as U.S. Pat. No. 7,087,058); Ser. No. 09/684,820 filed Oct. 10, 2000 (now issued as U.S. Pat. No. 6,558,386); Ser. No. 10/430,751 filed May 6, 2003; 60/182, 748 filed Feb. 16, 2000; Ser. No. 09/782,583 filed Feb. 13, 2001 (issued as U.S. Pat. No. 6,558,390); Ser. No. 09/848,556 filed May 3, 2001 (now issued as U.S. Pat. No. 7,014,633); Ser. No. 10/125,771 filed Apr. 18, 2002 (issued as U.S. Pat. No. 6,899,716); Ser. No. 10/990,705 filed Nov. 17, 2004 (now issued as U.S. Pat. No. 7,329,259); Ser. No. 10/430,841 filed May 6, 2003 (now issued as U.S. Pat. No. 7,309,338); Ser. No. 09/710,369 filed Nov. 10, 2000 (now issued as U.S. Pat. No. 6,740,090); Ser. No. 10/853,476 filed May 25, 2004 (now issued as U.S. Pat. No. 7,569,056); Ser. No. 09/709,105 filed Nov. 10, 2000 (now issued as U.S. Pat. No. 6,790,210); Ser. No. 09/782,534 filed Feb. 13, 2001; 60/513,899 filed Oct. 23, 2003; a series of applications filed Oct. 22, 2004: Ser. No. 10/971,779 (now issued as U.S. Pat. No. 7,530,993), Ser. Nos. 10/971,781, 10/971,731, 10/972,077 (now issued as U.S. Pat. No. 7,500,977), Ser. No. 10/971,765 (now issued as U.S. Pat. No. 7,473,256), Ser. Nos. 10/972,065, 10/971,775, 10/971, 780 (now issued as U.S. Pat. No. 7,588,574), Ser. No. 10/972, 184 (now issued as U.S. Pat. No. 7,717,958), Ser. No. 10,972, 039 (now issued as U.S. Pat. No. 7,491,236), Ser. No. 10,972, 040 (now U.S. Pat. No. 7,662,173), and Ser. No. 10/972,176 (now issued as U.S. Pat. No. 7,547,324); 60/558,069 filed Mar. 31, 2004; and 60/706,704 filed Aug. 9, 2005.

FIELD OF THE DISCLOSURE

The present disclosure relates generally to implantable device assemblies, instrumentation systems, and methods for accessing and achieving axial stabilization at multiple levels of the spine via a minimally-invasive trans-sacral approach (as described in U.S. Pat. No. 6,558,390 which is incorporated herein by reference) and subsequent therapeutic procedures, such as spinal arthroplasty; partial or total disc replacement; annulus repair, vertebroplasty; arthrodesis (fusion), or other spine-related procedures comprising the deployment of distal and proximal elongated implantable components and assemblies that can be used to position, manage motion, and stabilize a plurality of adjacent vertebral motion segments in the human spine to relieve lower back pain, restore physiological function of the lumbar spine, to maintain and possibly improve disc health, and prevent progression or transition of degenerative disease. More specifically, the present disclosure generally relates to the imposition of a sequence of two or more distractions on a set of two or more adjacent motion segments as part of the provision of therapy to the spine. Alternatively, the present disclosure includes methods of distracting a second, more caudal intervertebral disc space after placement of a therapeutic device for distraction and/or therapy of, or in, an adjacent distal motion segment. While the concept of distraction can be applied for moving one item apart from another in any dimension, in the context of this application and the claims that follow, distraction is considered in the orientation of the axes of the spinal column so that distraction elevates the height of, i.e., increases the distance between two adjacent vertebral bodies as measured in the direction of the longitudinal axis of the spine.

BACKGROUND

Overview

The present disclosure is an extension of work assigned to TranS1 Inc. with a principle place of business located in Wilmington, N.C. Much of the work is described in great detail in the many applications referenced above and incorporated by reference into this application. Accordingly, the background of the disclosure provided herein does not repeat all of the detail provided in the earlier applications, but instead highlights how the present disclosure adds to this body of work.

The spinal column is a complex system of bone segments (vertebral bodies and other bone segments) which are in most cases separated from one another by discs in the intervertebral spaces. FIG. 1 shows the various segments of a human spinal column as viewed from the side. Each pair of adjacent vertebral bodies and the intervertebral space contributes to the overall flexibility of the spine (known as a motion segment) and contributes to the overall ability of the spine to flex to provide support for the movement of the trunk and head. The vertebrae of the spinal cord are conventionally subdivided into several sections. Moving from the head to the tailbone, the sections are cervical 104, thoracic 108, lumbar 112, sacral 116, and coccygeal 120. The individual segments within the sections are identified by number starting at the vertebral body closest to the head. Of particular interest in this application are the vertebral bodies in the lumbar section and the sacral section. As the various vertebral bodies in the sacral section are usually fused together in adults, it is sufficient and perhaps more descriptive to merely refer to the sacrum rather than the individual sacral components.

The individual motion segments within the spinal columns allow movement within constrained limits and provide protection for the spinal cord. The discs are important to allow the spinal column to be flexible and to bear the large forces that pass through the spinal column as a person walks, bends, lifts, or otherwise moves. Unfortunately, for a number of reasons referenced below, for some people one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

A range of therapies have been developed to alleviate the pain associated with disc problems. One class of solutions is to remove the failed disc and then fuse the two adjacent vertebral bodies together with a permanent but inflexible spacing, also referred to as static stabilization. Fusing one section together ends the ability to flex in that motion segment. However, as each motion segment only contributes a small portion of the overall flexibility of the spine, it can be a reasonable trade-off to give up the flexibility of a motion segment in an effort to alleviate significant back pain.

Another class of therapies attempts to repair the disc so that it resumes operation with the intended intervertebral spacing and mechanical properties. One type of repair is the replacement of the original damaged disc with a prosthetic disc. This type of therapy is called by different names such as dynamic stabilization or spinal mobility preservation.

Generally, one of the first steps in providing either type of therapy (fusion or motion preservation) is to move adjacent vertebral bodies relative to one another (called distraction) to compensate for the reduction of intervertebral space attributed to the problems with the disc. Depending on the type of therapy that is to be delivered, it may be useful to separate the adjacent vertebral bodies by more than a normal amount of separation.

It is useful to set forth some of the standard medical vocabulary before getting into a more detailed discussion of the background of the present disclosure. In the context of the this discussion: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. As the present application contemplates accessing the various vertebral bodies and intervertebral spaces through a preferred approach that comes in from the sacrum and moves towards the head, proximal and distal are defined in context of this channel of approach. Consequently, proximal is closer to the beginning of the channel and thus towards the feet or the surgeon, distal is further from the beginning of the channel and thus towards the head, or more distant from the surgeon.

After the preceding primer on the subject, it is thought appropriate and useful to provide a more detailed discussion of the background of the disclosure.

Detailed Background of the Disclosure.

Chronic lower back pain is a primary cause of lost work days in the United States, and as such is a significant factor affecting both workforce productivity and health care expense. There are currently over 700,000 surgical procedures performed annually to treat lower back pain in the U.S. In 2004, it is conservatively estimated that there will be more than 200,000 lumbar fusions performed in the U.S., and more than 300,000 worldwide, representing approximately a $1B endeavor in an attempt to alleviate patients' pain. About 80% of the procedures involve the lower lumbar vertebrae designated as the fourth lumbar vertebra ("L4"), the fifth lumbar vertebra ("L5"), and the sacrum. In addition, statistics show that only about 70% of these procedures performed will be successful in achieving pain relief. Persistent lower back pain is generally "discogenic" in origin, i.e., attributed primarily to herniation and/or degeneration of the disc located between the L5-sacrum and/or the L4-L5 vertebral bodies in the lower lumbar section of the spine (See element 112 in FIG. 1).

Degeneration of the disc occurs when the intervertebral disc of the spine suffers reduced mechanical functionality due to dehydration of the nucleus pulposus. The nucleus pulposus provides for cushioning and dampening of compressive forces to the spinal column. In a healthy adult spine, the nucleus pulposus comprises 80% water. With age, the water and protein content of this tissue and the body's cartilage changes resulting in thinner, more fragile cartilage. Hence, the spinal discs and the facet joints that stack the vertebrae, both of which are partly composed of cartilage, are subject to similar degradation over time. The gradual deterioration of the disc between the vertebrae is known as degenerative disc disease, or spondylosis. Spondylosis is depicted on x-ray tests or MRI scanning of the spine as a narrowing (height reduction) of the normal "disc space" between adjacent vertebrae.

The pain from degenerative disc or joint disease of the spine may be treated conservatively with intermittent heat, rest, rehabilitative exercises, and medications to relieve pain, muscle spasm, and inflammation, but if these treatments are unsuccessful, progressively more active interventions may be indicated. In the context of the present disclosure, therapeutic procedures to alleviate pain and restore function are described in a progression-of-treatment from spinal arthroplasties, comprising prosthetic nucleus device implantation; annulus repair, and total disc replacement, to spinal arthrodesis, i.e., fusion, with or without concomitant device implantation.

Fusion involves a discectomy, i.e., surgical removal of the disc, followed by the subsequent immobilization of the two vertebral bodies, one superior and one inferior to the excised disc. Collectively, this unit of two vertebral bodies separated axially by a spinal disc, comprise a spinal motion segment. This procedure of discectomy and "fusion" of the vertebral bodies, i.e., so that the two vertebrae effectively become one solid bone, terminates all motion at that joint and is intended to eliminate or at least ameliorate discogenic pain. The benefit of fusion is pain relief and the down side is elimination of motion at the fused joint, which can hinder function. This surgical option is generally reserved for patients with advanced disc degeneration, and surgical procedures, such as spinal fusion and discectomy, may alleviate pain, but do not restore normal physiological disc function.

Moreover, traditional surgical fusion and other procedures that involve the removal of the herniated disc, e.g., with laminotomy (a small hole in the bone of the spine surrounding the spinal cord); laminectomy (removal of the bony wall); percutaneous discectomy (needle technique through the skin), or chemonucleolysis (disc-dissolving) generally have accessed the lumbo-sacral spine via direct, open exposure of the anterior or posterior segments, which limit and dictate the nature and design of instrumentation and implants used for site access and preparation; disc decompression (e.g., distract or elevate vertebral bodies in a motion segment to restore intervening disc height); fixation, and bone growth materials augmentation to facilitate the fusion process. Typical anterior or posterior surgical approaches and device interventions generally involve lateral screw fixation to the vertebral bodies of the lumbar spine and sacrum and various types of fasteners (rods, plates, etc.) that connect these screws together as one large construct. Such approaches also require muscle and ligament dissection, neural retraction, and annular disruption, i.e., are highly tissue invasive.

More recent anterior fixation systems have reduced the profile of these devices by locating their connector rods inside the anterior vertebral column instead of on the outside. In this manner, these systems may reduce or eliminate exposed surfaces for impingement of nerves, vessels, or soft tissue following implantation.

As an alternative therapy to spinal fusion, i.e., immobilization of the vertebral bodies within a motion segment, axial spinal mobility preservation devices (or herein, also termed motion management, or "MM" devices) generally introduced percutaneously through tissue to a trans-sacral access point on the spine in a minimally invasive, low trauma manner, to provide therapy to the spine, were disclosed in and commonly assigned U.S. Provisional Patent Application No. 60/558,069 filed Mar. 31, 2004, incorporated herein in its entirety into this disclosure by reference. The therapeutic advantage of the MM devices is to preserve mobility by restoring and managing motion via in situ dynamic device performance, and in a preferred aspect, the MM devices are assemblies that comprise a prosthetic nucleus (PN) component configured as an expandable membrane which is filled in situ, e.g., by injection or infusion of prosthetic nucleus material (PNM) with viscoelastic properties that assist in distraction (i.e., restoring disc height), and share and distribute physiologic loads among the physiologic structures of the vertebral motion segment, including distribution to the annulus and the inferior and superior vertebral bone end plates, so that biomechanical properties and function are optimized.

In order to overcome shortcomings or limitations associated with prior spinal devices and therapies, the present disclosure discloses novel axial spinal stabilization systems, comprising device assemblies and deployment instrumentation, that facilitate treatment among a plurality of vertebrae and motion segments at multiple levels of the spine, either by means of fixation or motion management constructs or via a combination of these therapies, which assemblies are introduced via a minimally invasive, pre-sacral access tract and trans-sacral axial surgical approach to the lumbo-sacral spine. More specifically, the axial rods and device assemblies are implanted preferably into the anterior vertebral column by means of device deployment instrumentation to systematically achieve novel means for multi-level axial spinal stabilization via therapeutic intervention or combination of interventions as indicated which selectively target multiple, adjacent motion segments to immobilize vertebral bodes and/or dynamically restore increased range of motion, improve biomechanical function, and provide discogenic pain relief.

In the context of the present disclosure, a "motion segment" comprises adjacent vertebrae, i.e., an inferior and a superior vertebral body, and the intervertebral disc space separating said two vertebral bodies, whether enucleated space or with intact or damaged spinal discs.

Axial Trans-Sacral Access.

Axial trans-sacral access to the lumbo-sacral spine as shown in FIG. 2, eliminates the need for muscular dissection and other invasive steps associated with traditional spinal surgery while allowing for the design and deployment of new and improved instruments and therapeutic interventions, including stabilization, mobility preservation, and fixation devices/fusion systems across a progression-of-treatment in intervention. More specifically, clinical indications for the multi-level axial spinal stabilization systems and the motion management assemblies described herein include patients requiring interventions to treat pseudoarthrosis, revisions of previous interventions, spinal stenosis, spondylolisthesis (Grade 1 or 2), or degenerative disc disease as defined as back pain of discogenic origin with degeneration of the disc confirmed by history and radiographic studies. The nature of specific assemblies selection by clinicians is dictated by multiple factors, e.g., individual patient age, anatomy, and needs within the progression-of-treatment options available, as well as in accordance with optimal intended function and in deference to biomechanical and safety constraints. FIG. 2 provides an introductory overview of the process with FIGS. 2A and 2B showing the process of "walking" a blunt tip stylet 204 up the anterior face of the sacrum 116 to the desired position on the sacrum 116 while monitored on a fluoroscope (not shown). This process moves the rectum 208 out of the way so that a straight path is established for the subsequent steps. FIG. 2C illustrates a representative axial trans-sacral channel 212 established through the sacrum 116, the L5/sacrum intervertebral space, the L5 vertebra 216, the L4/L5 intervertebral space, and into the L4 vertebra 220.

The use of a trans-sacral approach to provide spinal therapy is described in and commonly assigned U.S. patent application Ser. No. 10/309,416 which is incorporated by reference into this application. A brief overview of this method of accessing the spinal region to receive therapy is useful to provide context for the present disclosure. As shown in FIG. 2A, a pre-sacral approach through percutaneous anterior track towards sacral target, through which trans-sacral axial bore will be made and the access channel extended distally for subsequent advancement of multi-level axial spinal stabilization assemblies. An anterior, pre-sacral, percutaneous tract extends through the pre-sacral space anterior to the sacrum. The pre-sacral, percutaneous tract is preferably used to introduce instrumentation to access and prepare the access channel (e.g., by drilling a bore in the distal/cephalad direction through one or more lumbar vertebral bodies and intervening discs). "Percutaneous" in this context simply means through the skin and to the posterior or anterior target point, as in transcutaneous or transdermal, without implying any particular procedure from other medical arts. However, percutaneous is distinct from a surgical access, and the percutaneous opening in the skin is preferably minimized so that it is less than 4 cm across, preferably less than 2 cm, and, in certain applications, less than 1 cm across. The percutaneous pathway is generally axially aligned with the bore extending from the respective anterior or posterior target point through at least one sacral vertebral body and one or more lumbar vertebral body in the cephalad direction as visualized by radiographic or fluoroscopic equipment.

More specifically, as shown in FIG. 2B, the lumbar spine is accessed via a small skin puncture adjacent to the tip of the coccyx bone. The pre-sacral space is entered, using standard percutaneous technique, and the introducer assembly with the stylet's blunt tip serving as a dilator is placed through the paracoccygeal entry site. Once the tip of the stylet is through the facial layer, the blunt tip is rotated back against the anterior face of the sacrum and "walked" to the desired position on the sacrum under fluoroscopic guidance. Once the target site has been accessed and risk of soft tissue damage mitigated, the blunt-tipped stylet is removed and a guide pin, or wire, is safely introduced through the guide pin introducer tube, and "tapped in". The guide pin establishes the trajectory for placement of subsequent bone dilators and sheath through which a twist drill is introduced creating an axial bore track, the lumen of which is extended distally. The guide pin maintains the axial alignment of access and preparation tools as well as the alignment of cannulated spinal stabilization devices and assemblies, of larger diameter than the bore track, that are subsequently introduced over a 23" long, 0.090" diameter guide pin and through an exchange cannula for deployment within the vertebral column, as described at least in part in and commonly assigned U.S. patent application Ser. Nos. 10/972,065, 10/971,779, 10/971,781, 10/971,731, 10/972,077, 10/971,765, 10/971,775, 10/972,299, and 10/971,780, all of which were filed on Oct. 22, 2004, and in co-pending and commonly assigned United States Provisional Patent Application "Method & Apparatus for Access & Deployment of Spinal Stabilization Devices Through Tissue", filed Aug. 9, 2005, and all of which are incorporated by reference herein in their entirety.

As used herein, spinal arthrodesis is used in the context of fixation/fusion, leading to immobilization of two vertebral bodies within a motion segment, relative to one another. In the context of the present disclosure, "soft fusion" refers to immobilization by means of the introduction of bone growth facilitation/augmentation materials (e.g., osteogenic; osteoconductive media) without accompanying implantation of fixation devices (e.g., fusion rods).

In contrast, as used herein, the terms spinal arthroplasty and/or motion management encompass dynamic stabilization options for treating disc degeneration in a progression-of-treatment, i.e., when fusion is deemed too radical an intervention based on an assessment of the patient's age, degree of disc degeneration, and prognosis. More specifically, in the context of the present disclosure dynamic refers to non-static motion management devices inherently configured to allow mobility by enabling or facilitating forces or load bearing that assist or substitute for physiological structures that are otherwise compromised, weakened or absent. Mobility devices providing dynamic stabilization (DS) are provided across a progression-of-treatment for treating symptomatic discogenic pain, ranging from treatment in patients where little degeneration or collapse is evident radio-graphically, to those for whom prosthetic nucleus devices or total disc replacements are indicated. For example, a prosthetic nucleus (PN) would be indicated in patients with a greater degree of degeneration and loss of disc height but not to the stage where advanced annular break-down is present. A PN would go beyond DS by including an aggressive nucleectomy and subsequent filling of the de-nucleated space with an appropriate material. When introducing a prosthetic nucleus (including TDR—total disc replacement or PDR partial disc replacement), the goal is to restore, as opposed to preserve, disc height and motion. Total disc replacement (TDR) would be indicated with more advanced disease than with a PN but where some annular function remains.

In accordance with the present disclosure, therapeutic dynamic stabilization device assemblies are disclosed which provide, by design, resistance and limitation of motion in a controlled manner. As used herein, "resistance" refers to the force required to move through a full range of motion, whereas in contrast, "limitation" refers to not force but degree, i.e., curtailment of full range of motion in one or more directions. With respect to the lower levels of the lumbar spine, full range of motion comprises about 12 degrees of flexion, about 8 degrees of extension, about 4 degrees of left or right lateral bend, and about 2 degrees of clockwise or counterclockwise motion at each motion segment. Biomechanical properties of the mobility devices may be altered by design. For example, a flex coupler embodiment which supports a static load of about 100 lbs. at 1 mm deflection may be modified, by changing (reducing) the number of coils per turn, moving from a spring constant of about 2500 psi, or by altering "waist" diameter, i.e., the cross sectional area of the flexible mid-section of the device, which causes it to be stiffer, to withstand 200 lbs. at 1 mm deflection.

Thus, devices may be preferentially configured to comprise, for example, a mechanical stop(s) to limit motion, and/or resistance to motion, e.g., by varying cross-sectional area and hence stiffness, or other biomechanical properties relevant to preserving or restoring physiological function with respect to mobility. The assemblies may be constructed to provide full, unconstrained range of motion, semi-constrained range of motion where full range of motion is allowed in combination with increased resistance to motion, or limited range of motion wherein the extent of motion in one or more degrees of freedom is mechanically limited, with or without increased resistance to motion. More specifically, the spinal devices comprised in the inventive assemblies preferably selectively approximate the biomechanical properties (e.g., substantially matched bulk and compression modulus) of the physiological vertebral or disc structure(s) depending on the particular function(s) for which specific therapeutic procedure(s) are indicated.

In one aspect of the present disclosure, an axial spinal MM device comprises PN augmentation or replacement material, that provides the same load-bearing functions and characteristics as the natural disc nucleus and of the natural disc, said PN material contained within expandable membranes, comprised of elastomeric materials, e.g., silicone. Exemplary silicone is such as that obtained from Nusil Silicone Technology located in Carpeneria, Calif., exhibiting elongation of between about 500% and about 1500%, and most preferably at about 1000%, and having a wall thickness of 0.015" serve as a primary dynamic stabilization component, via load assimilation and load distribution, when filled and expanded via infusion or inflation with an appropriate material. In a further aspect of the present disclosure, the spinal MM device may be configured via engagement means as part of an inter-axial device assembly comprising a plurality of axial MM devices, or as assemblies comprising some combination of axial MM device(s) and axial fixation rod(s). In a preferred aspect, this is achieved by means of axial deployment of devices with an aspect ratio of greater than 1, i.e., the device dimension in the axial vertebral plane is greater than the device dimension in any orthogonal direction to that axial plane in close proximity to the physiological instantaneous center of axial rotation.

As used herein, the term "axial rod" refers to axially deployed spinal implants which are fabricated, for example, by machining from metal, cylindrical (i.e., rod-like) solid blanks, and said term may encompass fixation/fusion or motion management devices as indicated, since the specific nature, form and function of such devices are determined by/dependent upon final implant configuration. The fabrication, forms, and function of various implant configurations of axial spinal motion management devices to preserve or restore mobility are disclosed in and commonly assigned U.S. patent application Ser. Nos. 10/972,184, 10/972,039, 10/972,040, and 10/972,176, all of which were filed on Oct. 22, 2004 the contents of which are hereby incorporated in their entirety into this disclosure by reference.

The axial rods serve multiple purposes, including but not limited to, modifying the height between the bodies, assuming physiological axial loads, providing access for the introduction of osteogenic and/or osteoconductive materials, and precluding device expulsion by means of anchoring. For example, the method of using the distraction/fusion rod generally comprises the steps of: determining the desired change in disc height between targeted vertebral bodies; selecting a rod with the appropriate thread pitches in the distal and proximal sections to achieve the desired change in height; accessing the targeted bodies by creating an axial bore that extends in the distal (cephalad) direction from a target point on the anterior surface of the sacrum to the disc space between the targeted bodies; extending the axial bore in the distal direction to create an extended portion of the axial bore, wherein the extended portion has a smaller diameter than the portion of the axial bore extending from the sacral target point to the disc space between the targeted bodies; and advancing and implanting the selected rod into the targeted bodies to achieve the desired change in disc height. Moreover, when devices and assemblies are anchored in bone to eliminate migration and expulsion they are preferably configured with self-tapping, bone anchoring threads configured to distribute stress evenly over a large surface area. The threads are typically of "cancellous" type bone threads known in the art. More specifically, they are typically but not exclusively cut with generally flat faces on the flights of the thread with the flattest of the faces oriented in the direction of the applied load.

There are a number of parameters that can be used to describe a set of threads. A set can be male or female A set of threads can be right handed or left handed. The number of threads per unit length (pitch) can be varied from one set of threads to another. The minor and major diameters of the threads can be varied from one set of threads to another. A more subtle difference is that form of the threads—the shape of a cross section of a thread can vary from one set of threads to another (such as V-shaped threads or buttress threads). For the purposes of this application and the claims that follow, one set of threads is said to be the same type as another set of threads when all of these parameters are the same such that the another set of threads can be rotated into a thread path cut by the first set of threads without needing to cut a new thread path (if the another set of threads is keyed or timed to place the another set of threads into the proper position to start into the previously cut thread path).

In a preferred aspect of the disclosure, stop flow means such as an axial rod plug are used to preclude leakage or migration of the prosthetic nucleus material either through an axial spinal dynamic stabilization rod or from the intervertebral disc space. As will become apparent from the accompanying figures and as used herein, "assembly" may refer, in context, to a single implant which when fully deployed within the spine comprises at least two distinct parts that are configured and engaged in and referred to as an intra-axial alignment, for example, an axial rod and an axial rod plug internally engaged and axially aligned within (i.e., longitudinally) said axial rod. Additionally, again in context, "assembly" may refer to the combination of a plurality of single-part implants and/or two part intra-axial devices-assemblies, such as just described above, which are configured with engagement means enabling constructs as inter-axial components that collectively comprise an integrated unit or assembly, for example, a distal component rod or rod-assembly as the distal implant in engagement along the center line of a longitudinal axis and axially aligned with a proximal component rod or rod-assembly, as the proximal implant wherein the two components collectively comprise a two-level axial stabilization assembly for two adjacent motion segments, e.g., L4-L5 (distal) and L5-sacrum (proximal).

In a preferred aspect of the present disclosure, multi-level axial stabilization assemblies are configured from two components: a distal component rod, comprising a threaded distal end with a first thread pitch and a threaded proximal end with a second, different thread pitch (hereinafter referred to as dissimilar thread pitches); and a proximal component rod, comprising a distal end that is a tapered and non-threaded cylinder and a threaded proximal end comprising tapered distal threads; said component rods (with or without accompanying intra-axially engaged rod plugs) which are sequentially deployed by means of instrumentation and methods as will be described below, as fixation implants in adjacent motion segments, e.g., first in L4-L5 (superior/distal component rod) and then L5-sacrum (inferior/proximal component rod), respectively; so that the subsequent engagement of the distal end of the proximal component rod internally within and in inter-axial alignment with the proximal end of the distal component rod forms a two-level, spinal axial stabilization assembly that enables independent (adjusted) axial distraction (an extension/increase in height, resulting in disc decompression and pain relief) of both the proximal and distal intervertebral discs spaces, respectively, within two adjacent motion segments.

In particular, the axial configuration of the anchors (i.e., self-tapping threads) allows the proximal and distal thread profiles of the distal component rod to be of different pitch. Thread pitch, as used herein, is defined as the distance between corresponding points on consecutive threads, i.e., threads per inch or TPI. This design using dissimilar thread pitches allows each end of the rod to screw into the superior and inferior vertebral bodies of the L4-L5 motion segment at independent rates resulting in distraction of the two vertebrae and an increase in disc height without the need for additional "distracting" instrumentation as is required in other arthrodesis. Moreover, the degree or amount of distraction to be achieved, for example from between about 1 mm to about 10 mm and often between about 2 mm and 6 mm, may be selected by pre-determining the variability in thread pitch between the threaded distal and proximal ends.

The use of dissimilar thread pitches to distract vertebral bodies within a single motion segment is described in commonly assigned U.S. Pat. No. 6,921,403 "Method and Apparatus for Spinal Distraction and Fusion" issued on Jul. 26, 2005 which is incorporated herein in its entirety by reference into this disclosure. However, in a further inventive aspect of the present multi-level stabilization system, in order to enable adequate and simultaneous distraction and subsequent therapy of a second motion segment (proximal) disc space, the proximal component rod needs only to be threaded at its proximal end as described in the preceding paragraph, so that as its threads engage the proximal vertebral body said component is both anchored and advanced into the proximal disc space until its distal end subsequently engages the distal component rod's proximal end, effectively comprising an integral implant assembly. In this manner, distraction of the proximal disc space is thereafter achieved by means of force applied, in the distal direction, to the proximal end of the distal component subsequent to said engagement of the two components, so that the distal end of the proximal component will push against and lift the proximal end of the distal component.

In one aspect of the disclosure, the device assemblies are configured to mechanically and adjustably, distract multiple disc spaces and configured to be deployed so as to be oriented in approximately the line of principal compressive stress, i.e., the device is configured to be placed at approximately the center of rotation in a human disc motion segment. In turn, this yields a more uniform, radial distribution of loads to more closely approximate physiological load sharing.

In accordance with this aspect of the present disclosure, the axial stabilization devices disclosed herein are less likely to cause the phenomena of subsidence and transition syndrome. As used herein, subsidence refers to the detrimental descent of an orthopedic implant into bone that surrounds it. Transition syndrome refers to altered biomechanics and kinematics of contiguous vertebral levels and concomitant risk of adjacent motion segment instability that may occur as a result of spinal therapeutic procedures that are suboptimal in terms of their ability to restore physiological function and properties, and thus risk a cascading deleterious effect on surrounding otherwise healthy tissue.

Applicants believe the advantage of adjusting distraction between and among successive adjacent vertebral bodies within multiple motion segments at various spinal levels, as just described, of the inventive multi-level axial stabilization assembly systems described herein to be unique, i.e., that no other (known) current spinal therapies are able to achieve across a plurality of adjacent motion segments distraction/decompression and stabilization/motion management, including combinations of progression-of-treatment options, leading to discogenic pain relief.

Thus, it is one object of the present disclosure to provide device-assemblies and deploy them in a method that independently increases intervertebral disc height within a first motion segment and a second, adjacent motion segment.

It is another object of the present disclosure to provide spinal axial stabilization system assemblies as disclosed herein that restore normal intervertebral disc height by distracting vertebral bodies within and among a plurality of adjacent motion segments, and to achieve mechanical stability of the joint by augmenting or replacing prosthetic nucleus material to distribute physiologic loads and/or managing motion in said spinal segments to eliminate chronic pain.

It is another object of the present disclosure to preserve biomechanical function and eliminate chronic pain by facilitating successful fusion of motion segments within multiple levels of the spine by means of axially-deployed, differentially threaded (anchored) spinal fixation assemblies that provide adjustable distraction to restore normal intervertebral disc height among a plurality of adjacent motion segments and that achieve stabilization in closer proximity to the instantaneous center of rotation around the vertical axis of the spine, advantages not afforded by other current spinal fusion systems.

It is a further object of the present disclosure to provide axial spinal devices and assemblies, as well as instrumentation and methods for their deployment, which collectively comprise an axial spinal stabilization system, in particular, for the anterior lumbar spine, capable of distracting and treating multiple vertebral bodies and adjacent motion segments at multiple levels of the spine via fixation; motion management; or both static and dynamic stabilization, by means of a minimally invasive, pre-sacral surgical approach and trans-sacral deployment and axial orientation of the spinal devices and assemblies through the vertebral bodies, in a manner that does not compromise the annulus and adjacent tissues. More specifically, yet another advantage of the present disclosure is the concurrent implementation of a combination of therapies, i.e., deployment of spinal assemblies are disclosed that enable dynamic stabilization via implantation of one or more prosthetic nucleus devices or other mobility preservation/restoration devices, such as those disclosed and described previously in and commonly assigned U.S. patent application Ser. Nos. 10/972,184, 10/972,039, 10/972,040, and 10/972,176, all of which were filed on Oct. 22, 2004 incorporated herein in their entirety into this disclosure by reference, as alternative options to or together with fixation rods facilitating fusion of the vertebral bodies, to selectively achieve motion management rather than elimination of motion with respect to a targeted plurality of motion segments within multiple spinal levels.

MM devices (also referred to as mobility devices) decompress the disc and alleviate pain caused by nerve impingement, usually posterior, by means of either inducing slight segmental kyphosis (introduction of added convex curvature through increasing the height on the posterior side of the disc more than on the anterior side of the disc) or straight elevation, and by creating limits and resistance to segmental motion. In this manner, devices are able to provide both stable anterior and posterior load support (e.g., loads that may approximate 10 times the body weight of a patient) and adequate medial-lateral and rotational support, without adjunctive posterior instrumentation and without accompanying osteogenesis.

Certain of the dynamic stabilization devices of the present disclosure comprise a flexible member in between more rigid distal and proximal threaded anchor portions. The flexible member, which may comprise a cable, spring, flexible coupler, stacked-washers, inflatable bladder (e.g., expandable membrane), or a combination thereof, serves as a "shock absorber", and is able to assimilate forces or redistribute loads. Hence, in accordance with this aspect of the present disclosure, the mobility device assembly comprising one or more flexible member(s), in combination with at least one anchor portion(s), may be configured from among these design concepts and embodiments, including: helical flexure (flexible coupler) designs, comprising one-piece or two-piece devices that may be configured with or without an integral, elastomeric or elastic inflatable, i.e., expandable, membrane that serves to maximize surface area over which loads are distributed, and that may or may not assist in distraction; cable designs, comprising one piece of fixed length, with or without an inflatable membrane, or two or more parts of variable length; ball and track multi-part designs; "stacked washer" designs, and anchored nuclear replacements.

It is another object of the present disclosure to provide a spinal PND (prosthetic nucleus device) which preferably does not impede the mobility of, and is responsive to the physiological ICOR (instantaneous center of rotation). Moreover, in one aspect, the PND provides anterior-posterior translation and has a mobile ICOR. The PNDs of the present disclosure do not adversely impact the stiffness of the motion segment being treated. For example, PND axially deployed in the L5-sacrum lumbar spine enable/accommodate range of motion of between about 10° to 15° flexion; between about 7° to about 10° extension; about 5° of left or right lateral bending and between about 1° to about 2° clockwise or counterclockwise axial rotation, while those implanted in L4-L5 enable/accommodate range of motion of between about 8° to 10° flexion; between about 5° to about 7° extension; between about 5° to about 7° left or right lateral bending; and between about 1° to about 4° clockwise or counterclockwise axial rotation.

In a preferred aspect of the disclosure, the overall length of, for example of the proximal component (L5-Sacrum) of the MM device-assembly ranges from about 40 mm (size small) to about 60 mm (size large), and the expandable membrane component may be folded within a cannulated section of the mobility device during device delivery to the target site, and then deployed, e.g., unfolded, in situ via expansion by infusion or inflation into the (denucleated) intervertebral disc space of the L5-Sacrum motion segment.

Thus, preferential vertebral body positioning, distraction and decompression, and static or dynamic stabilization are achieved by interventions which at the same time mitigate surgical risks associated with traditional, conventional procedures, e.g., bleeding, neurological damage, damage to soft tissue, spinal cord impingement or damage and infection, and, additionally, provide an improved level of clinical biomechanical performance compared with conventional spinal components and techniques for spinal arthrodesis or arthroplasties on multiple levels within the spinal column.

It is further believed that in addition to providing devices and assemblies that can mechanically eliminate or limit acute pathologic motion and establish long-term stability of spinal segments by immobilizing or significantly managing the range of motion of the segment, inherent risks associated with implant breakage, loosening or expulsion of the implants possibly causing delayed nerve root impingement or damage, fracture of osseous structures, and bursitis, are substantially reduced with respect to the present inventive axial assemblies, as are pain, discomfort or abnormal sensations due to the presence of the device.

For example, another advantage of the inventive spinal axial stabilization system is that deployment and orientation present no exposed surfaces for impingement of nerves, vessels, or soft tissue. Additionally, due to the axial delivery of the implant via a protected channel, there is no retraction of muscles and no exposure to major vessels or soft tissue as with the delivery system for systems delivered from other surgical approaches.

This is the case whether the method of implant deployment is by an anterior (preferred), or a posterior approach, and it will be understood that references to anterior approaches, while preferred, are for convenience only, and that both pre-sacral anterior and posterior approaches and subsequent trans-sacral axial stabilization methods and devices afford significant advantages over current practice, including: the patient is in a prone position that is easily adaptable to other posterior instrumentation; blood loss is minimal; soft tissue structures, e.g., veins, arteries, nerves are preserved, and substantially less surgical and anesthesia time is required compared with conventional procedures; the implants of the present disclosure are intended to preserve or restore function, not merely alleviate pain.

The objects, advantages and features of the present disclosure presented above are merely exemplary of some of the ways the disclosure overcomes difficulties presented in the prior art, and are not intended to operate in any manner as a limitation on the interpretation of the disclosure. These and other advantages and features of the multi-level axial stabilization devices and assemblies, as well as the surgical tools sets and techniques for their deployment, disclosed in the present disclosure will be more readily understood from the following summary and a detailed description of the preferred embodiments thereof, when considered in conjunction with the accompanying figures.

SUMMARY OF THE DISCLOSURE

Previous work has developed a range of fusion and mobility maintenance (MM) therapeutic devices for use in the intervertebral space between the L5 and sacrum. In some instances there may be a need to provide therapy to both the L5/sacrum intervertebral space but also to the adjacent superior L4/L5 space and to do so in a manner that requires independent control over the amount of distraction applied to each space. In some instances there may be a need to provide distraction and then therapy to more than two adjacent intervertebral spaces such as L3/L4, L4/L5, and L5/sacrum. Further, even if it were possible to perforin a sequence of single distractions using axial rods of the type described above for single level distraction (as there are challenges to placement of two different rods in the medial of the three vertebral bodies), there may be advantages to providing various forms of mechanical interaction between the axial rods for two adjacent intervertebral spaces.

The previously unfulfilled needs to provide therapy to two or more adjacent motion segments accessed through a trans-sacral approach are addressed by the present disclosure. Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

BRIEF DESCRIPTION OF THE FIGURES

FIG. 5 shows one embodiment of a proximal distraction rod;

FIG. 8 shows yet another plug embodiment that uses a separate plug within the proximal rod that does not connect the proximal rod to the distal rod;

FIG. 9 presents a flow chart for the process of imposing two distractions on adjacent intervertebral spaces;

FIG. 14 shows a preferred driver for insertion or removal of plugs as this driver has a retention rod to engage the plug to the distal tip of the driver.

DETAILED DESCRIPTION

As the present disclosure is an extension of earlier work by TranS1 Inc. that has been well documented by a series of patent applications that have been incorporated by reference, this discussion will focus on the aspects of the disclosure that are new and the particularly relevant aspects of the previously described work that are useful for explaining the new material. The general method for establishing a channel via a trans-sacral approach has been well documented and is generally applicable to the present disclosure as the inventive axial spinal stabilization rods and assemblies disclosed in this application are deployed via substantially the same trans-sacral access, using preparations, methods, and surgical tools and instrumentation sets described previously in and commonly assigned U.S. patent application Ser. Nos. 10/972,065, 10/971,779, 10/971,781, 10/971,731, 10/972,077, 10/971,765, 10/971,775, 10/972,299, 10/971,780, all of which were filed on Oct. 22, 2004, and in and commonly assigned United States Provisional Patent Application "Method & Apparatus for Access & Deployment of Spinal Stabilization Devices Through Tissue," filed Aug. 9, 2005, as U.S. Provisional Pat. App. No. 60/706,704, all of which are incorporated herein by reference in their entirety.

As noted previously, all steps in this surgical technique use active real time imaging, and preferably by radio-imaging means such as biplane fluoroscopy, and generally the inventive axial rods of the present disclosure are cannulated for delivery of device assemblies by means of deployment over an extended guide pin, for an atraumatic introduction through soft tissue through an exchange cannula that has been advanced into its proper target location. Those interested in the details of these preparatory steps can review and commonly assigned U.S. Provisional Application No. 60/601,842 filed Aug. 14, 2004 for Method & Apparatus for Multi-Level Stabilization of the Spine including pages 21-27 which are incorporated herein by reference. Another discussion of relevant preparations can be found in commonly assigned U.S. Pat. No. 6,921,403 "Method and Apparatus for Spinal Distraction and Fusion" issued on Jul. 26, 2005 the relevant portions are incorporated herein by reference.

Figure 1:
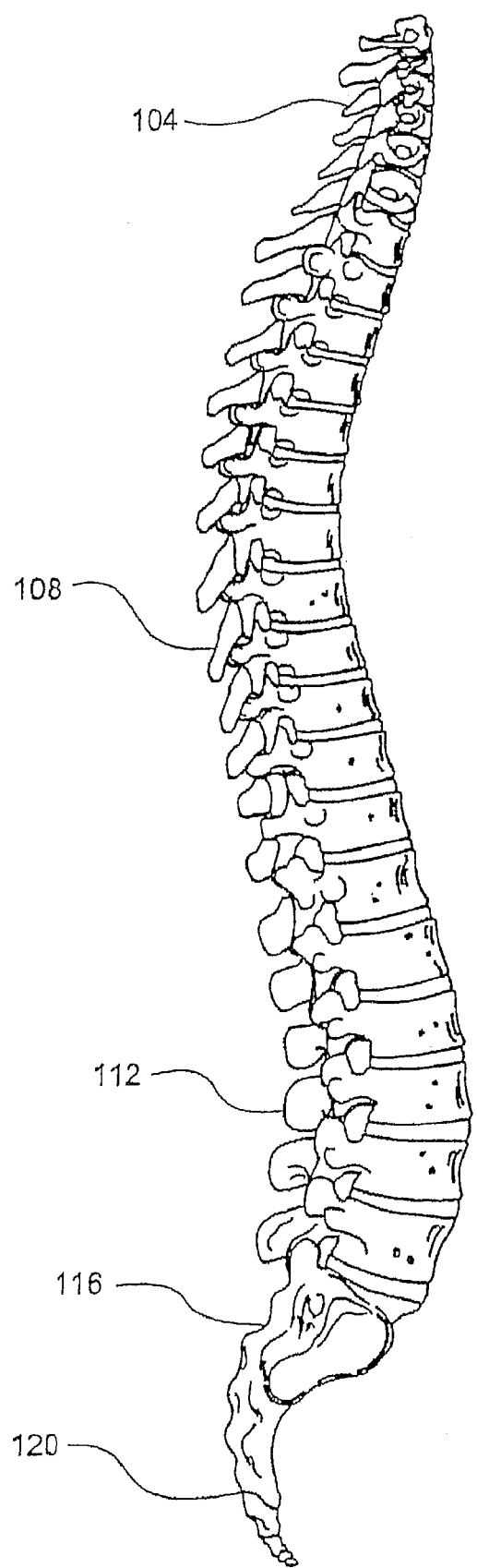
FIG. 1 is a side view of a human spine.
Figure 2A:
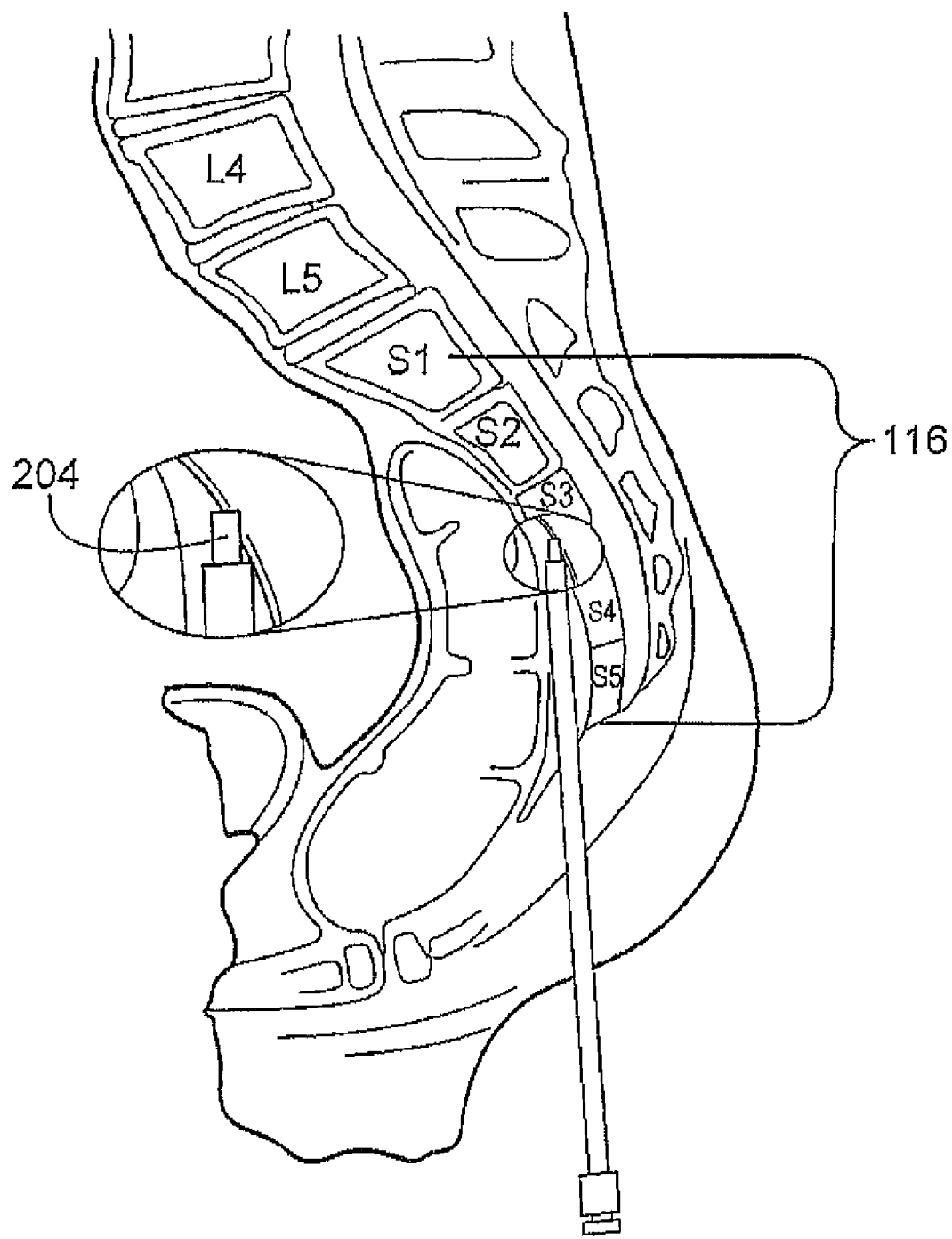
FIGS. 2A, 2B, and 2C show a trans-sacral approach and the formation of a channel for receipt of therapeutic devices.
Figure 2B:
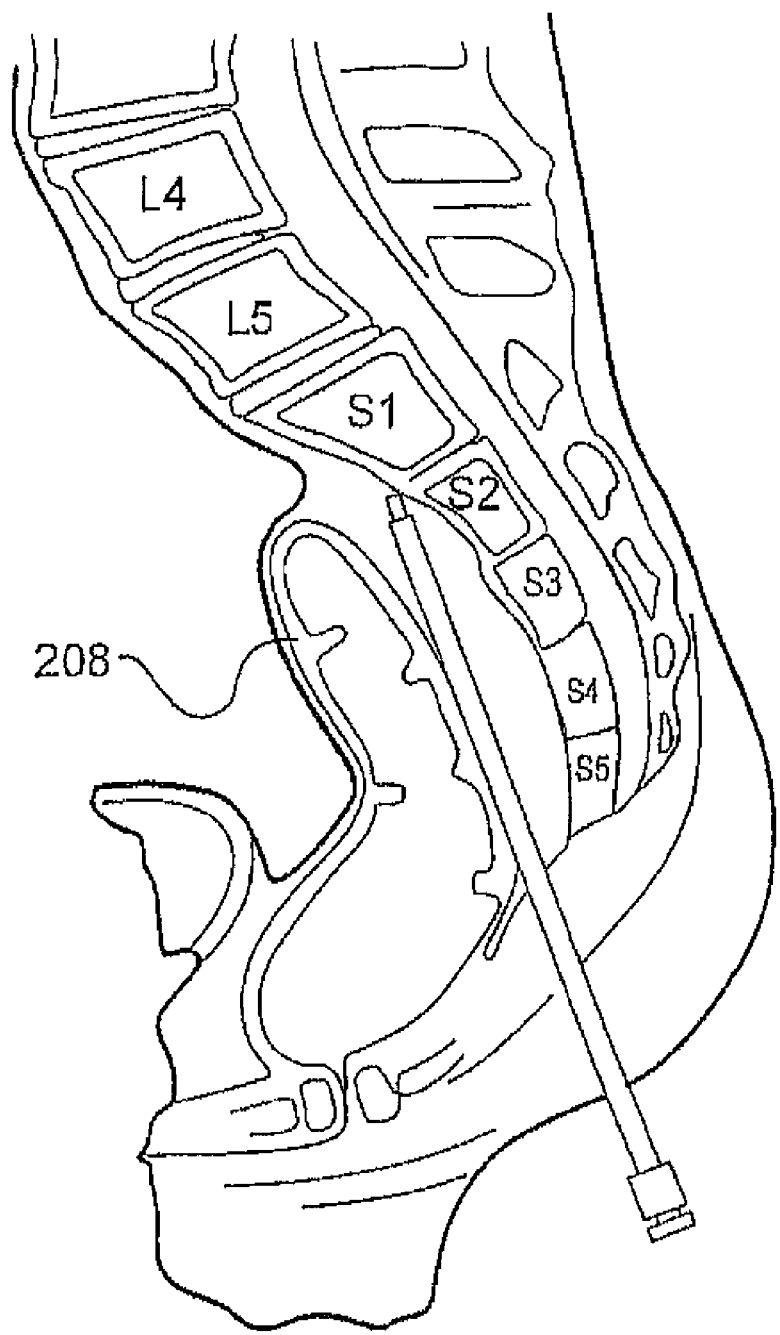
Figure 2C:
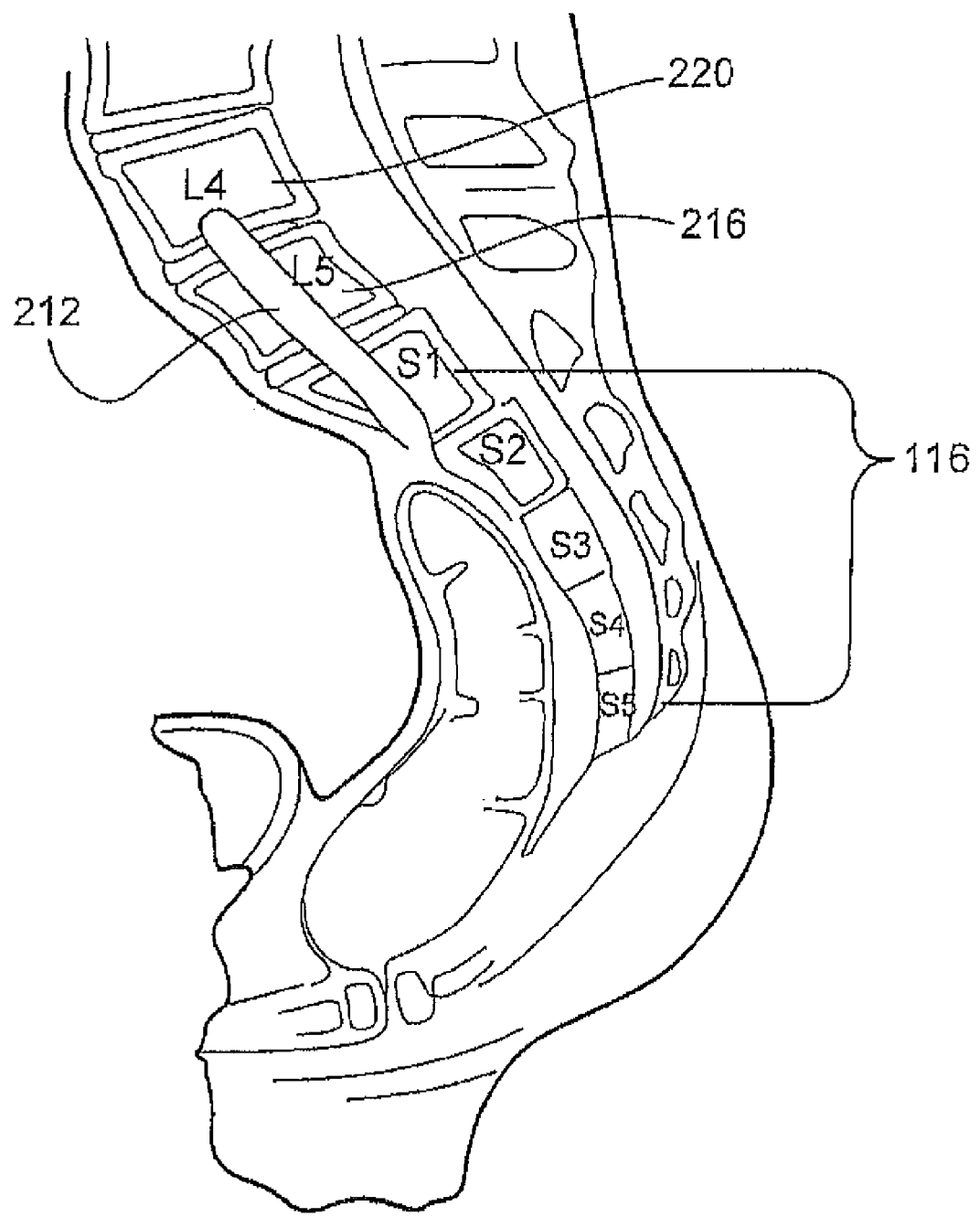
Figure 3:
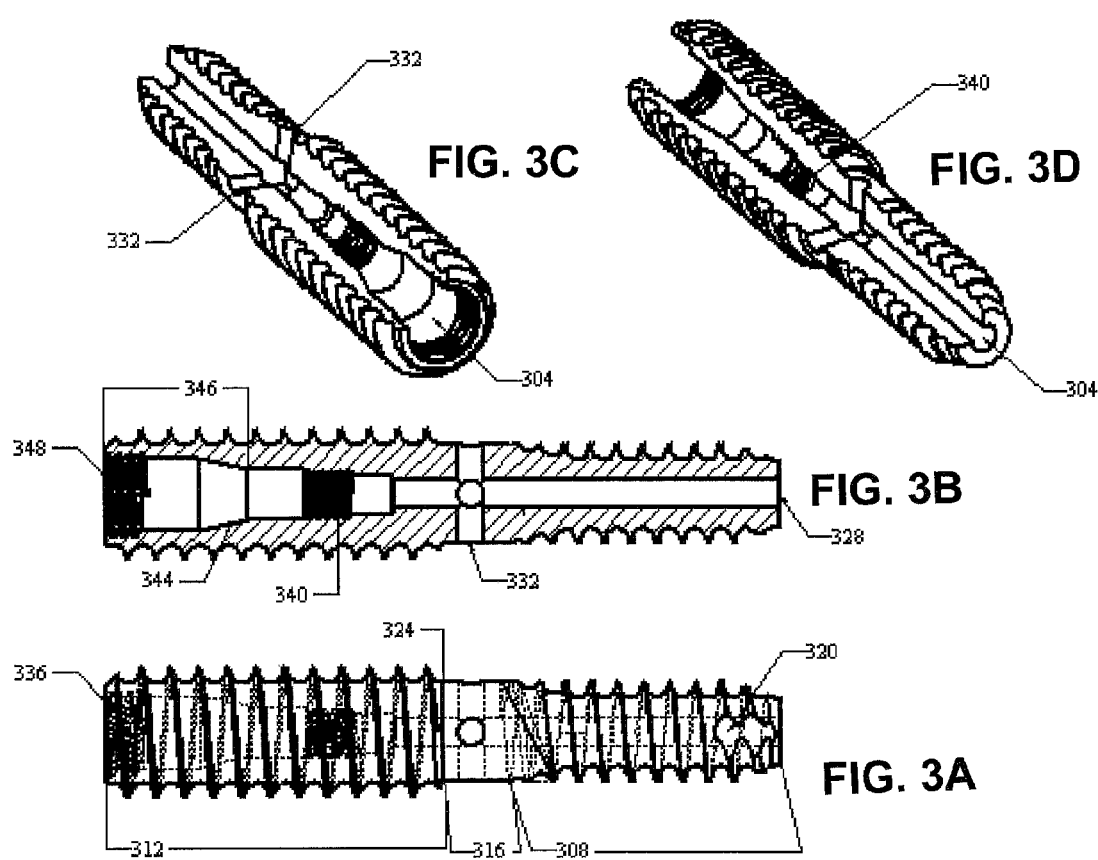
FIG. 3 shows one embodiment of a distal distraction rod.
Figure 4:
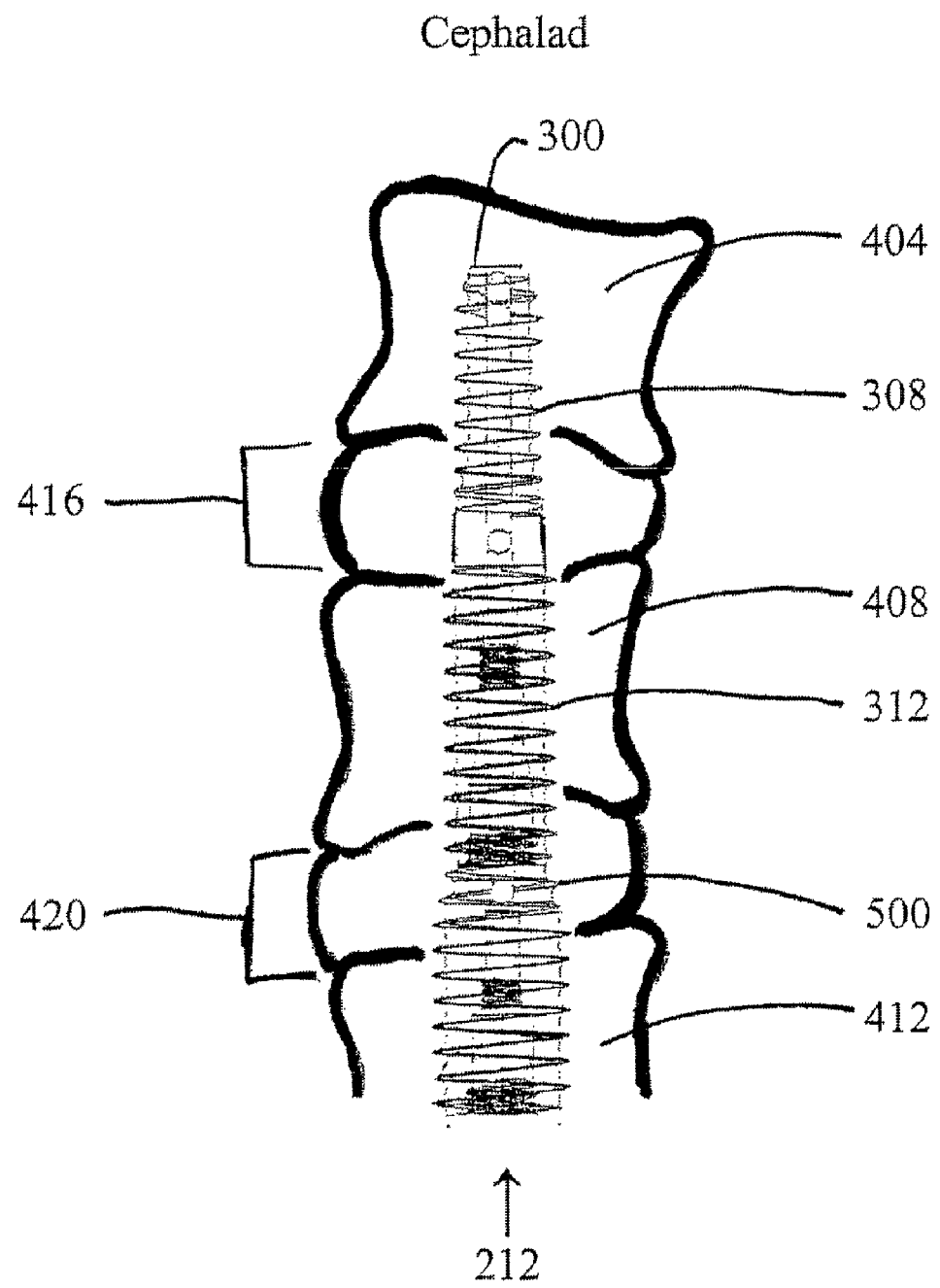
FIG. 4 shows an installed assembly with a distal distraction rod and a proximal distraction rod.

FIG. 3 shows one embodiment of an exemplary distal distraction rod 300 in accordance with the present disclosure. (As will be discussed in greater detail below, the disclosure is not limited to situations where the distal device is anchored in two different vertebral bodies or even if so anchored, is used to impose a distraction.) FIG. 3A shows the exterior, FIG. 3B provides a cross section, and FIGS. 3C and 3D provide solid surface views in perspective with a longitudinal section removed to expose the interior cavity 304. The operation of the distal distraction rod is best explained in connection with spinal components as shown in FIG. 4. FIG. 4 shows three adjacent vertebral bodies called herein distal vertebral body 404, medial vertebral body 408, and proximal vertebral body 412. The three vertebral bodies define two adjacent motion segments, comprising intervertebral disc spaces, the distal intervertebral disc space 416 and the proximal intervertebral disc space 420. Note that the proximal vertebral body is drawn without a complete outline as the three vertebral bodies are not meant to be limited to specific vertebral bodies. Thus, the proximal vertebral body 412 is not necessarily the sacrum 116 in FIG. 2C as the axial trans-sacral channel 212 may have been extended sufficiently into the spine so that the most distal vertebral body 404 is L3 or higher.

The distal axial rod 300 is comprised of a distal threaded section 308, a proximal threaded section 312 and in this preferred embodiment, a waist section 316. The use of dissimilar thread pitches allows for the controlled distraction of two vertebral bodies (FIG. 4 elements 404 and 408) when the distal threaded section 308 is engaged with a distal vertebral body 404 and the proximal threaded section 312 is engaged with the medial vertebral body 408.

The use of dissimilar thread pitches to distract vertebral bodies within a single motion segment is described in copending and commonly assigned U.S. patent application Ser. No. 10/309,416 filed on Dec. 3, 2002, now U.S. Pat. No. 6,921,403 which is incorporated herein in its entirety by reference into this disclosure. The use of dissimilar thread pitches can be used in the distal axial rod 300 which is advanced into the vertebral bodies (404 and 408) by rotating the trailing end of the distal axial rod in the same direction as the "handedness of the screw". The thread on the proximal threaded section 312 and the thread on the distal threaded section 308 both extend counterclockwise (or both clockwise) around the elongate body comprising the device, and preferably the distal and proximal threads are self-tapping. A distal axial rod 300 having a thread pitch in its distal threaded section 308 that is finer relative to the thread pitch in the threaded proximal section 312 causes distraction of the intervertebral disc space 416 between the two engaged vertebral bodies 404 and 408 as each turn of the distal axial rod 300 in the proper direction with respect to handedness of the threads will move the distal axial rod 300 relative to the distal vertebral body 404 a first amount but the distal axial rod 300 will move relative to the more proximal vertebral body 408 (medial vertebral body) a larger amount. The ratio of the first amount to the larger amount will be proportional to the ratio of the pitch of the distal threaded section to the pitch of the proximal threaded section. One of skill in the art can appreciate that in order to effect a more significant distraction; one would select more significantly dissimilar thread pitches than the combination shown in FIG. 3. As rotation in one direction causes distraction, rotation in the opposite direction causes compression.

The preferred embodiments of distal axial rod 300 include a chip breaker section 320 to facilitate screwing the distal end of the distal distraction rod into the distal vertebral body. The leading edge 324 of the thread for the proximal threaded section grows from the minor diameter to the major diameter of the threaded section. The cavity 304 of the distal distraction rod 300 includes several apertures 332 that extend radially outward at the waist 316. These apertures can be used to deliver material as part of providing therapy to the motion segment, including bone paste or other materials to promote fusion. The distal end 328 of cavity 304 is not generally used as an aperture for delivery of therapeutic material as this distal end 328 would be positioned in a vertebral body rather than in an intervertebral space. The opening at the distal end 328 is useful when deploying the distal distraction rod over a guide wire.

Note that if the major diameter of the threads in the distal threaded section 308 is less than the minor diameter of the threads in the proximal threaded section 312 then the channel prepared for the insertion of the distal distraction device can be of a smaller cross section as the channel enters the distal vertebral body than the cross section of the channel through the medial vertebral body such that the distal section of the distal distraction device can pass through the medial vertebral body without having to be screwed through. While this may appear attractive to pass the distal threaded section through the medial vertebral body in that the bone around the channel is not marred or otherwise weakened, this is not a preferred practice. A preferred practice is to use a sequence of decreasing major diameters, but not necessarily to the extent that the more distal thread sets can be passed through without rotating the rod.

It has been found that the engagement of a first set of threads with a major diameter that is small relative to the size of the bore through the vertebral body but yet engages the bore through a vertebral body does not adversely impact the ability to thread a subsequent set of threads that have a larger major diameter into that same vertebral body. The advantage of not stepping down the major diameters to such a significant degree that one set of threads can pass through another more proximal bore in a vertebral body without screwing the threaded rod through the bore is that the range of thread sizes is less extensive. An extensive range of thread sizes when using three or more sets of threads forces a choice between using rods that have distal sections that are relatively thin or ending with rods that are very thick.

Rod driver engaging zone 336 can be made in one of several configurations known to those of skill in the art to allow a driver to impart rotation to the rod. For example, the proximal end of the distal distraction rod 300 can be fitted with a female hex head suitable for driving with a driver having a corresponding male hex head. A suitable driver is described in priority document No. 60/601,842 filed Aug. 14, 2004 for Method & Apparatus for Multi-Level Stabilization of the Spine and the relevant portions of that document including FIG. 28 are incorporated herein by reference.

In a preferred embodiment the distal distraction rod 300 may be configured to have a set of female extraction threads 348 (for example left-handed metric thread pattern M7) within the proximal end of the cavity 304. The thread matches the thread on an extraction driver tool.

It is likely that the process to extract a previously inserted rod would start with using the driver to rotate the rod in the counterclockwise direction to start the extraction of the previously inserted rod. (In some cases the extraction could be performed without the initial involvement of the driver to start the disengagement.) Once the distal distraction rod is backed out slightly with an axial rod driver tool that engages with the rod driver engaging zone 336, the extraction tool can be used to engage the female extraction threads 348 and pull the distraction rod out the rest of the way, if there is a need for such extraction, e.g., in the event of revision or implant selection resizing. The use of left-handed threads is preferred as this allows the extraction of the engaged right-handed threads of the rod to be disengaged by rotating the extraction tool in the normal counterclockwise direction. By using left-handed threads, counterclockwise rotation will cause the left-handed threaded section of the distal tip of the extraction tool to engage with corresponding threads on the rod to be extracted. After the left-handed threads are fully engaged, further rotation of the extraction tool in the counterclockwise direction will disengage the right-handed threads on the rod from the vertebral body. Once the rod is disengaged from the vertebral body, it can be pulled out with the tip of the extraction tool as it will be engaged with the left-handed threads of that tool.

In a particularly preferred embodiment, the left-handed threads are cut into the polygonal walls of the rod driver engagement zone (perhaps best seen in FIG. 6B described below). The use of extraction tools with left-handed threads to remove a rod is not limited to distal distraction rods, but can be used for any installed device that is engaged with right-handed threads including plugs (described below). One of skill in the art will appreciate that if the devices are engaged into vertebral bodies or into other devices using left-handed threads for the engagement, then an extraction tool would have right-handed threads so that clockwise rotation of the extraction tool would disengage such a device.

The use of female extraction threads has been discussed in connection with a distal distraction rod 300 as an example of this aspect of the present disclosure, but the concept is applicable to other axially inserted devices.

FIG. 5 shows an exemplary proximal distraction rod 500 for use with the present disclosure. More specifically, FIG. 5A shows the exterior of the proximal distraction rod 500; FIG. 5B shows a cross section along the length of the proximal distraction rod 500; and FIG. 5C provides a solid surface perspective view of the proximal distraction rod 500 with a longitudinal segment removed. Proximal distraction rod 500 is comprised of a threaded section 504 and an engagement section 508. While not shown in this embodiment, one of skill in the art could reduce the length of the threaded section so that the threaded section ends before the beginning of the engagement section, e.g., by including a waist as seen in the exemplary distal distraction rod 300.

The threaded section 504 has a tapered section 512 and a straight section of thread 516 as this configuration facilitates threading the leading edge of the threaded section into the proximal vertebral body 412.

The engagement section is not threaded but has a tapered leading edge 520. As the proximal distraction rod 500 is advanced in the channel, the tapered leading edge 520 of the engagement section 508 engages with the proximal end of the distal distraction rod 300. The engagement section 508 proceeds into the distal distraction rod cavity 304 until the shoulder 524 of the proximal distraction rod presses against the trailing edge of the distal distraction rod 300.

In a preferred embodiment, the distal engagement section 508 of the proximal distraction rod essentially fills the corresponding portion 346 ("engagement zone") of the bore in the distal distraction rod 300. In one embodiment the specification for the bore size for the portion to receive the cylindrical shank is 0.250 inches (+0.005 inches, −0.000 inches) and the specification for the dimension of the cylindrical shank is 0.2495 inches (+0.000 inches, +0.005 inches). The angle used for the tapered leading edge 520 portion of the distal engagement section 508 is repeated in the corresponding section of the bore 304.

This close fit of the leading portion of the proximal distraction rod 500 with the trailing portion of the bore 304 in the distal distraction rod serves to maintain the axial alignment of the two rods to one another while retaining the ability for the proximal distraction rod 500 to rotate relative to the distal distraction rod 300 without imparting a rotation to the distal distraction rod and thus altering the previously imposed distal distraction. The rotation of the proximal distraction rod 500 with threads engaged in the proximal vertebral body 412 advances the proximal distraction rod 500 which pushes on the distal distraction rod 300 to push the distraction rod and the engaged distal 404 and medial 408 vertebral bodies away relative to the proximal vertebral body 412 to impose a desired amount of distraction of the proximal intervertebral disc space 420.

Note that with the method as described, the amount of distraction imposed on the proximal intervertebral disc space 420 is independent of the amount of distraction imposed on the distal intervertebral disc space 416. Note further, that the pitch of the thread on the threaded portion 504 of the proximal distraction rod is not relevant to the amount of distraction that can be imposed (beyond changing the amount of distraction per turn of the distraction rod). In fact, the handedness of the thread for the threaded portion 504 of the proximal distraction rod can be chosen independent of the handedness of the thread used for the proximal distraction rod so that distraction is imparted by rotating the distal distraction rod in a first direction and distraction is imposed by rotating the proximal distraction rod in the opposite direction.

Optionally, the cross section of the proximal distraction rod 500 can be selected to be sufficiently larger than the major diameter of the proximal threaded section 312 of distal distraction rod 300 to allow the cross section of the channel formed in proximal vertebral body 412 to be sized so that the distal distraction rod 300 can be passed through the proximal vertebral body 412 without being screwed through it or otherwise marring the bone surface exposed by the channel.

Proximal distraction rod 500 has a set of apertures 532 connected to the cavity 528 of the proximal distraction rod 500. These apertures can be used to distribute therapeutic material as part of the procedure of motion segment fusion. In a preferred embodiment, there are four apertures spaced 90 degrees apart.

Rod driver engaging section 536 can be made in one of several configurations known to those of skill in the art to allow a driver to impart rotation to the rod. For example, the proximal end of the proximal distraction rod 500 can be fitted with a female hex head suitable for driving with a driver having a corresponding male hex head. A suitable driver is described in priority document No. 60/601,842 filed Aug. 14, 2004 for Method & Apparatus for Multi-Level Stabilization of the Spine and the relevant portions of that document including FIG. 28 are incorporated herein by reference.

A set of female extraction threads 548 (preferably left-handed metric threads) at the proximal end of the bore of the proximal distraction rod 500 can be used for the extraction of the proximal distraction rod as discussed in connection with female extraction threads 348.

Female threaded section 540 for use in securing a bore plug in the cavity 528 will be discussed in greater detail below.

Cavity Plugs.

The purpose of the axial rod plug is to preclude leakage or migration of the osteogenic, osteoconductive, or osteoinductive gel or paste which is inserted by means of an augmentation media (e.g., bone paste; PN material) inserter through apertures from the cavity of the distal or proximate distraction rods into the intervertebral spaces as part of the process of promoting fusion or for other therapeutic purposes. Often the material inserted in this way is intended to fill available volume not occupied, e.g., by previously introduced autologous bone graft material, in its entirety. In a preferred aspect of the present disclosure, the plug is fabricated from the same titanium alloy as the axial rod, although it may be formed from other suitable (e.g., biocompatible; polymeric) materials.

A) Interlocking Cavity Plugs.

Figure 6A:
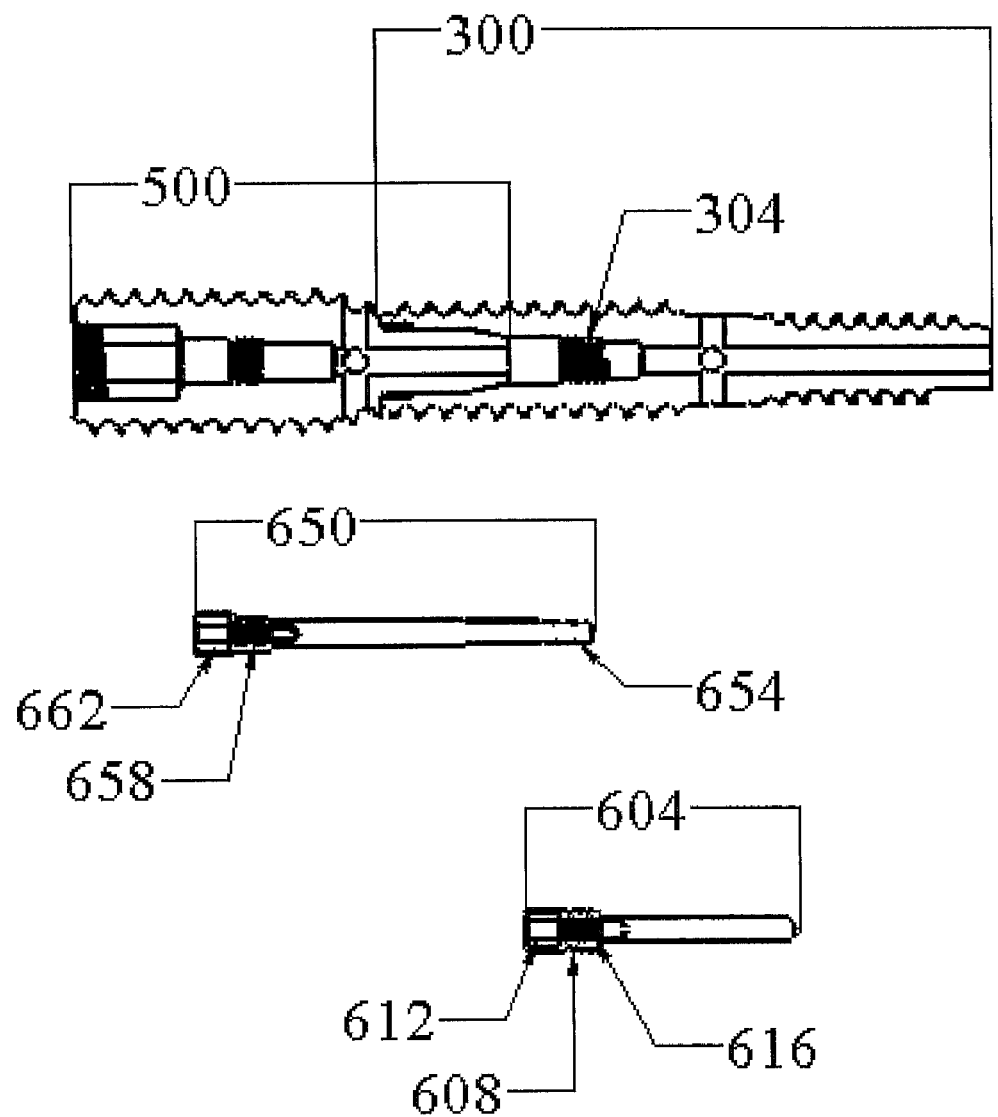
FIG. 6A shows an assembly of a distal distraction rod and a proximal distraction rod along with optional plugs.

FIG. 6A presents a representation of a distal distraction rod 300 with a proximal distraction rod 300 shown inserted into the proximal end of the cavity of the distal distraction rod. As noted above, the cavity 304 of the distal distraction rod is connected to apertures 332 and it may be desirable to plug the cavity 304 to prevent or limit the ingress of material into the cavity 304 including the post-treatment ingress of therapeutic material delivered through these apertures. A distal rod plug 604 is shown (not to scale) with a male threaded section 608 that corresponds to female threaded section 340. The distal rod plug 604 can be driven by a hex driver that is appropriately sized to drive a female hex fitting 612 in the trailing edge of the cavity in the distal rod plug 604. A suitable driver is described in priority document No. 60/601,842 filed Aug. 14, 2004 for Method & Apparatus for Multi-Level Stabilization of the Spine and the relevant portions of that document including FIG. 29 are incorporated herein by reference. The distal rod plug 604 when installed in the distal distraction rod 300 is seated distal to the tapered section 344 of the cavity so that the installed distal rod plug does not interfere with the insertion of the proximal distraction rod 500 into the proximal end of the distal distraction rod 300.

The cavity in the distal rod plug 604 has a female threaded section 616 which will be described in connection with the proximal distraction rod plug 650.

Proximal rod plug 650 has male threaded section 654 which is adapted to engage female threaded section 616 of distal rod plug 604 to bind together the assembly including distal distraction rod 300 with distal rod plug 604 along with proximal distraction rod 500 to provide one rigid assembly. Note that in the preferred embodiment, the proximal rod plug 650 does not engage via male threads with female threaded section 540 in the proximal end of the cavity of the proximal distraction rod 500. By not engaging with a second set of threads in a different axial rod that is free to rotate with respect to the distal rod, there is no risk of cross-threading or working out an alignment method to align the female threaded sections to one another.

Proximal rod plug 650 in turn has an axial cavity with a female threaded section 658. This threaded cavity is used in connection with a preferred plug driver described below that uses a retention rod to engage with the plug so that it remains engaged with the distal tip of the driver until the driver is disengaged from it.

The proximal rod plug 650 can be driven by a hex driver that is appropriately sized to drive a female hex fitting 662 in the trailing edge of the cavity in the proximal rod plug 650. A suitable driver is described in priority document No. 60/601, 842 filed Aug. 14, 2004 for Method & Apparatus for Multi-Level Stabilization of the Spine and the relevant portions of that document including FIG. 29 are incorporated herein by reference.

Figure 6B:
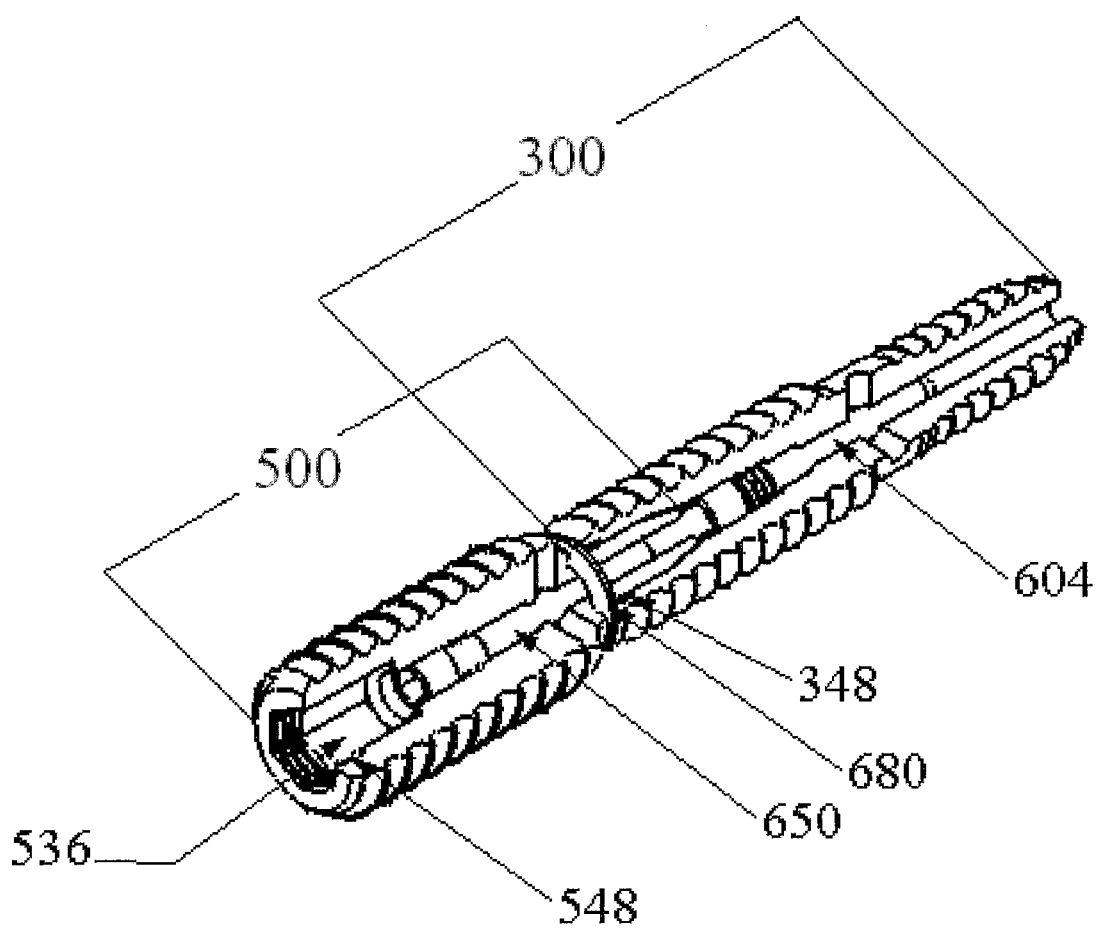
FIG. 6B shows a quarter-round cut-away perspective drawing of an assembly with a thrust bearing 680.

FIG. 6B shows a perspective view with a quarter section removed of an assembled combination of a proximal rod 500, a distal rod 300, a distal rod plug 604 and a proximal rod plug 650 that engages with the proximal end of the distal rod plug 604. Note that the components have been sized to allow for the use of a thrust bearing 680 which serves to facilitate (e.g., lubricate) the rotation of the proximal rod 500 against the distal rod 300 so that the proximal rod can advance and rotate without imparting rotation to the previously installed distal rod 300.

The thrust bearing can be as shown here as a washer shaped structure. As the thrust bearing will be placed inside a human body, it should be made of a biocompatible material and tolerant of the forces it may see in use. As the thrust bearing is meant to facilitate the rotation of the more proximal rod 500 relative to the more distal rod 300 while under an axial load, the coefficient of sliding friction between the thrust bearing and the rod moving relative to the thrust bearing should be less than the coefficient of sliding friction between two rods as shown in FIG. 6A.

An example of a material considered appropriate for the thrust bearing is ultra high molecular weight polyethylene (UHMWPE) another viable but less preferred material is polyether ether ketone known as PEEK.

The perspective view shown in FIG. 6B includes the female extraction threads 348 for the distal distraction rod 300 and a better view of the female extraction threads 548 for the proximal distraction rod 500. Note in the preferred embodiment the female extraction threads such as 548 are cut into the most proximal section of a polygonal rod driver engaging section 536.

B) Single Trans-Rod Plug.

Figure 7:
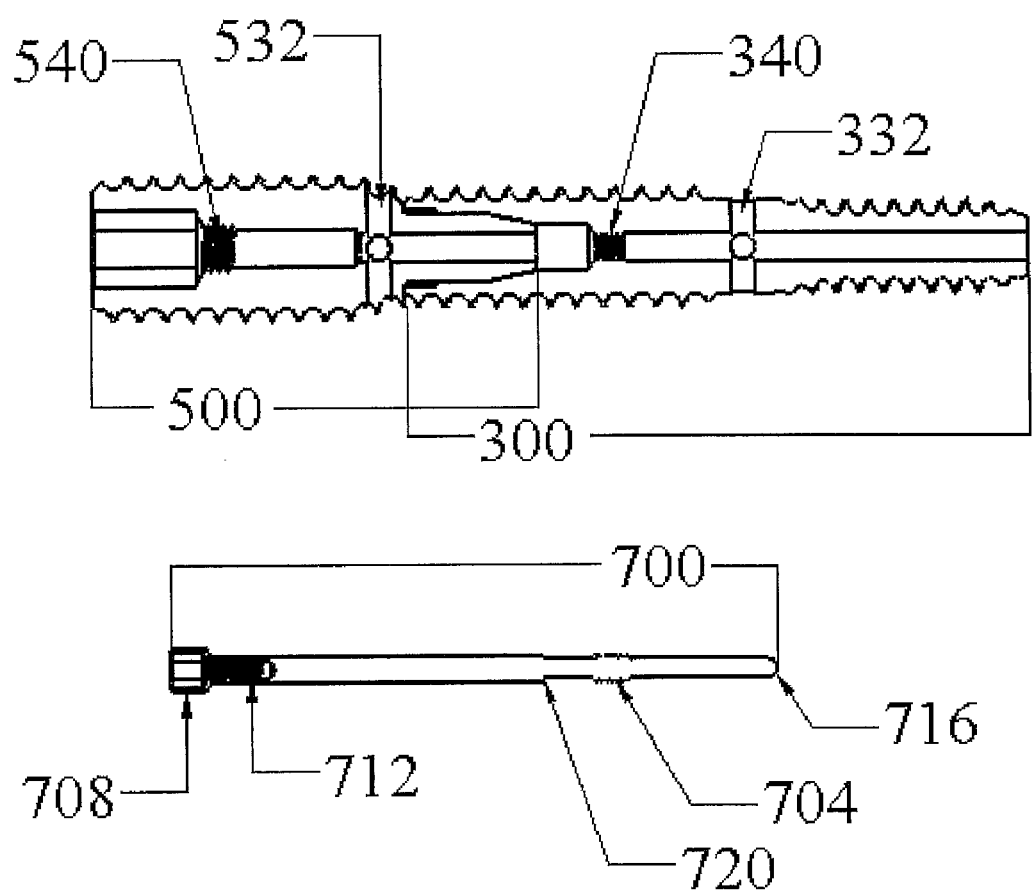
FIG. 7 shows another plug that joins the distal and proximal rods.

An alternative embodiment of the present disclosure uses a single plug, but uses one that locks together the distal distraction rod 300 with the proximal distraction rod 500. Plug 700 has a male threaded section 704 that is adapted to engage with female threaded section 340 when an appropriate driver (not shown in FIG. 7) presses upon and rotates the plug through interaction at female socket 708. The cavity of plug 700 has female threaded section 712. When fully inserted, the tip 716 of plug 700 is beyond the apertures 332 so as to block the ingress of material back through those apertures or through apertures 532 of the proximal distraction rod.

In certain situations the pair of plugs 604 and 650 may be preferable to plug 700 as the insertion of distal rod plug 604 seals off the apertures 332 before the proximal distraction.

C) Two Independent Plugs.

FIG. 8 illustrates a third embodiment in which the ingress of material into the proximal distraction rod 500 is limited by the use of a plug 804 that is engaged with the proximal distraction rod 500 rather than the distal distraction rod 300 or a plug within distal distraction rod 300. More specifically, FIG. 8A shows a partial cross section and FIG. 8B shows a side-elevational perspective view of a proximal distraction rod 500 inserted into the proximal end of a distal distraction rod 300. The distal distraction rod 300 is sealed internally with a plug 804 and a proximal rod plug 850 is located in the proximal distraction rod 500. In each case, a male threaded section 808 and 858 engage corresponding female threaded sections 340 and 540 (best seen in FIG. 6) to secure the plug (804 or 850) into the cavity of the distraction rod. The plugs are driven by appropriate drivers that engage the engagement sections 812 and 862 (preferably female hex fittings). The tips 816 and 866 of the plugs are placed so that material cannot travel from the apertures back into the longitudinal cavities of the distraction rods.

There are advantages in reducing the number of different unique parts in configuring the distraction rods such that a single plug could be used in either the proximal or distal distraction rods and in using the same plug for a range of different length distraction rods (or in the case of the distal distraction rod for distraction rods with different pairings of proximal and distal thread pitches).

Flow Chart.

After the introduction of the various components and concepts set forth above, it may be helpful to review the presented material through the context of a flowchart. FIG. 9 presents a flow chart for the process of imposing two distractions on adjacent intervertebral spaces.

Step 905 calls for preparation of the channel to allow for the insertion of the axial distraction rods.

Step 910 calls for engaging the threads from the distal threaded section 308 with the distal vertebral body 404 and the proximal threaded section 312 with the medial vertebral body 408.

Step 915 calls for rotating the engaged distal distraction rod 300 by applying force to the rod driver engaging zone 336 to selectively impose a specific amount of distraction to the distal intervertebral space through the action of the differences in thread pitch between the distal threaded section 308 and the proximal threaded section 312. Note that the direction of rotation to impose a distraction is a function of the handedness of the threads and whether the finer pitch thread is on the proximal or distal set of threads.

Step 920 calls for applying the desired therapy to the distracted distal intervertebral space 416. This therapy may include providing materials to the distal intervertebral space 416 through the apertures 332.

Step 925 calls for the optional addition of a distal distraction rod plug such as distal distraction plug 604. This is optional as some medical providers may opt to not seal the cavity at all and some may rely on a plug applied after the proximal distraction that will seal both axial distraction rod cavities.

Step 930 calls for threading the proximal distraction rod 500 into the proximal vertebral body 412.

Step 935 calls for rotating the proximal distraction rod 500 until it pushes against the engaged distal distraction rod to impose a specific amount of distraction upon the proximal intervertebral disc space 420. Preferably the distal end of the proximal distraction rod 500 engages with the proximal end of the cavity in the distal distraction rod 300 so that the application of force by the proximal distraction rod 500 against the distal distraction rod 300 occurs without disturbing the axial alignment of the two distraction rods. Note that the amount of distraction imposed on the proximal intervertebral disc space is not dependent on the amount of distraction imposed on the distal intervertebral space.

Step 940 calls for the application of the therapy to the proximal intervertebral disc space 420 which may include the insertion of material into the proximal intervertebral space through the apertures 532.

After the application of the therapy to the proximal intervertebral space there are several options for the application of a plug. One option not explicitly set forth on the flow chart is to not insert any plug at all in the proximal distraction rod. Steps 945, 950, and 955 provide alternatives that can be selected to insert three different types of plugs into the proximal distraction rod.

Step 945 calls for the addition of a proximal distraction rod plug such as shown in FIG. 8 as element 850. Such a plug seals the cavity of the proximal distraction rod but does not serve to join the proximal distraction rod 500 with the distal distraction rod 300 (either directly or indirectly through a distal plug).

Step 950 calls for the insertion and engagement of a proximal distraction plug with the distal distraction rod 300. This was illustrated by element 700 in FIG. 7 which engages with the female threaded section 340 in the distal distraction rod 300.

Step 955 calls for the insertion and engagement of a proximal distraction plug with the distal distraction rod plug such as is shown in FIG. 6 as proximal distraction rod plug 650 engages with previously inserted distal distraction rod plug 604 to provide added stability by joining the proximal distraction rod 500 to the distal distraction rod 300.

Note that when discussing the plugs referenced in Steps 950 and 955 and when focused on the structural contributions of such plugs, it is perhaps more appropriate to refer to the device as an inter-rod connector as one of ordinary skill in the art can appreciate that an inter-rod connector provides a function of connecting the two rods together whether or not sealing is desired or even provided by the inter-rod connector. Thus, a connector between two axial distraction rods in keeping with the teachings of the present application are intended to be within the scope of the claims whether or not such a connector serves a purpose of acting as a "plug" to limit the ingress of material into the cavity through an aperture as some distraction rods may not have apertures and some therapies may not call for the insertion of therapeutic material through the apertures.

Distraction of Three or More Adjacent Intervertebral Spaces.

Figure 10:
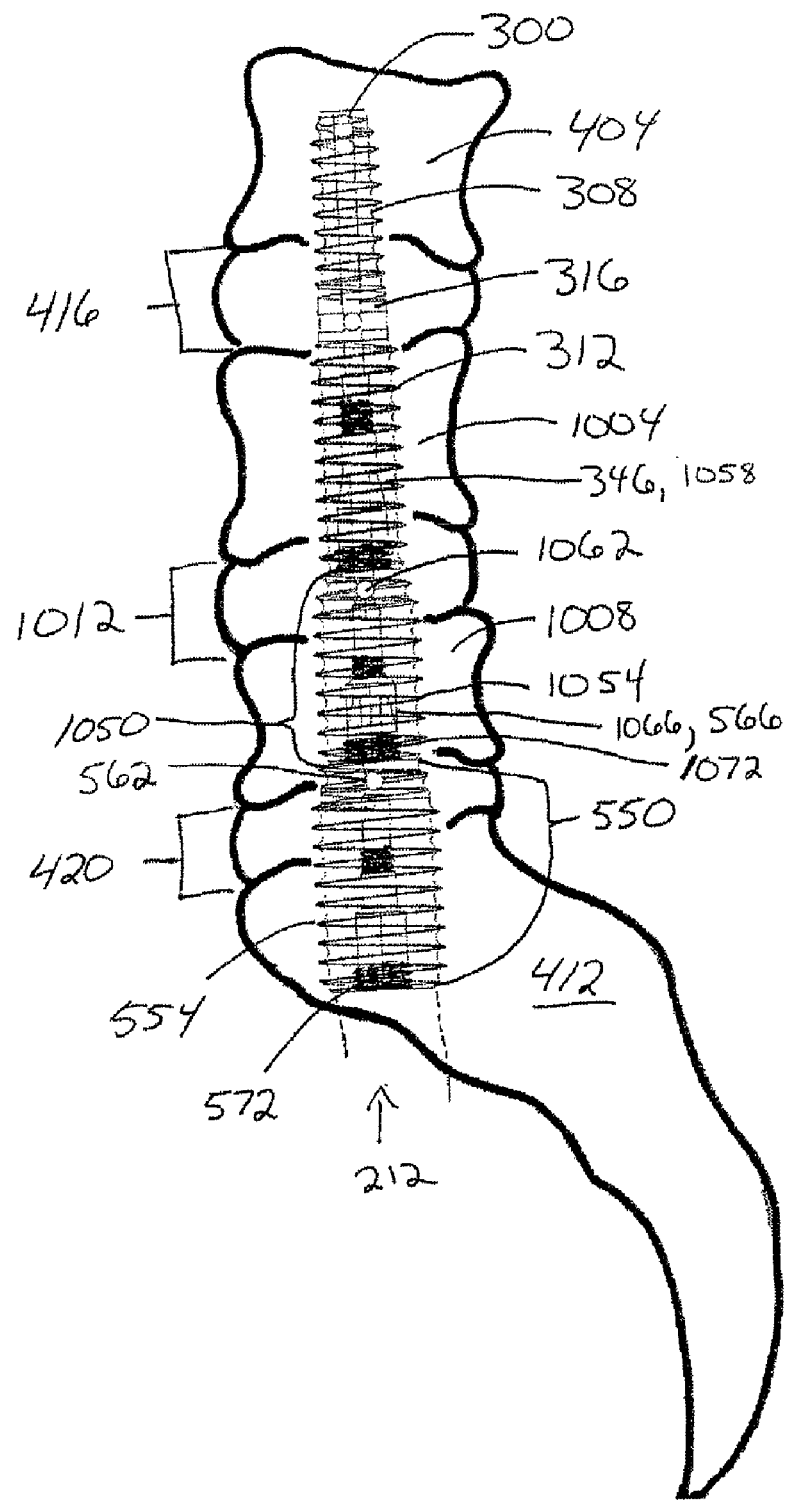
FIG. 10 illustrates the use of the present disclosure for a situation calling for the consecutive therapy of three adjacent motion segments.

FIG. 10 illustrates the use of the present disclosure for a situation calling for the consecutive therapy of three adjacent motion segments The three rod assembly is shown in outline but includes indications of aspects of the interior cavities including threads, engaging sections for rod drivers and the engagement zones and engagement sections such as engagement zone 346 of the distal distraction rod 300 and the corresponding engagement section 1058 of the next distraction rod (described below).

In this case the four vertebral bodies illustrated in FIG. 10 are the distal vertebral body 404 (L3), distal-medial vertebral body 1004 (L4), proximal-medial vertebral body 1008 (L5), and proximal vertebral body 412 (sacrum). The three intervertebral disc spaces between the four vertebral bodies are the distal intervertebral disc space 416, the medial intervertebral disc space 1012, and the proximal intervertebral disc space 420. This embodiment has three axial distraction rods, the distal distraction rod 300, a medial distraction rod 1050, and a proximal distraction rod 550.

The insertion of the distal distraction rod 300 to distract the distal intervertebral disc space 416 through the use of two sets of threads of different pitches operates as described above. Naturally, the lengths of the distal threaded section 308, proximal threaded section 312, and waist 316 will be adjusted to be appropriate for whatever motion segment is targeted whether it is L3/L4 instead of L4/L5.

As the threaded section 1054 of the medial distraction rod 1050 engages the proximal-medial vertebral body 1008, continued rotation applied through an engagement between a driver and a corresponding rod driver engagement zone in the proximal cavity of the medial distraction rod causes the medial distraction rod 1050 to advance and push against the proximal end of the distal distraction rod 300. This advancement and pushing causes an enlargement of the intervertebral space, in this case the medial intervertebral disc space 1012. After the distraction, the apertures 1062 are positioned in the intervertebral space so that therapeutic material can be delivered to this space.

In a preferred embodiment the distal end of the medial distraction rod 1050 will have an engagement section 1058 that fits with close tolerances within the engagement zone 346 proximal end of cavity 304 within the distal distraction rod 300.

The medial distraction rod 1050 is characterized by having an engagement section 1058 to engage with a correspondingly shaped portion of a cavity of a more distal rod and an engagement zone 1066 in a portion of the cavity at the proximal end of the medial distraction rod 1050 that is adapted for receiving the engagement section 566 of a more proximal distraction rod. In short, the medial distraction rod 1050 is adapted to push against a more distal distraction rod and to be pushed by a more proximal distraction rod. In keeping with the description set forth in connection with the distractions rods shown in FIGS. 3 and 5, the medial distraction rod 1050 would also include a rod driver engagement zone in the proximal end of the cavity for use by a corresponding driver and may include female threads 1072 for use by an extraction tool.

A proximal rod 550 is subsequently threaded into the proximal vertebral body 412. The proximal rod 550 in this embodiment has apertures 562 in fluid communication with the internal cavity of the proximal distraction rod 550. The proximal distraction rod 550 would also include a rod driver engagement zone in the proximal end of the cavity for use by a corresponding driver and may include female threads 572 for use by an extraction tool.

While the two examples given above in connection with FIGS. 4 and 10 show a series of fusion therapies applied to two or three adjacent motion segments, the disclosure is not limited to fusion therapy. Another class of therapies works to provide for some degree of post-operative mobility in the treated motion segment. The specifics of the therapeutic aspects of such devices have been described in detail in the earlier applications referenced above. As the focus of this application is on the ability to provide therapy to two or more adjacent motion segments, the details of the operation of these axial spinal mobility preservation devices (also termed dynamic stabilization or motion management, or "MM" devices) are not repeated here.

Figure 11:
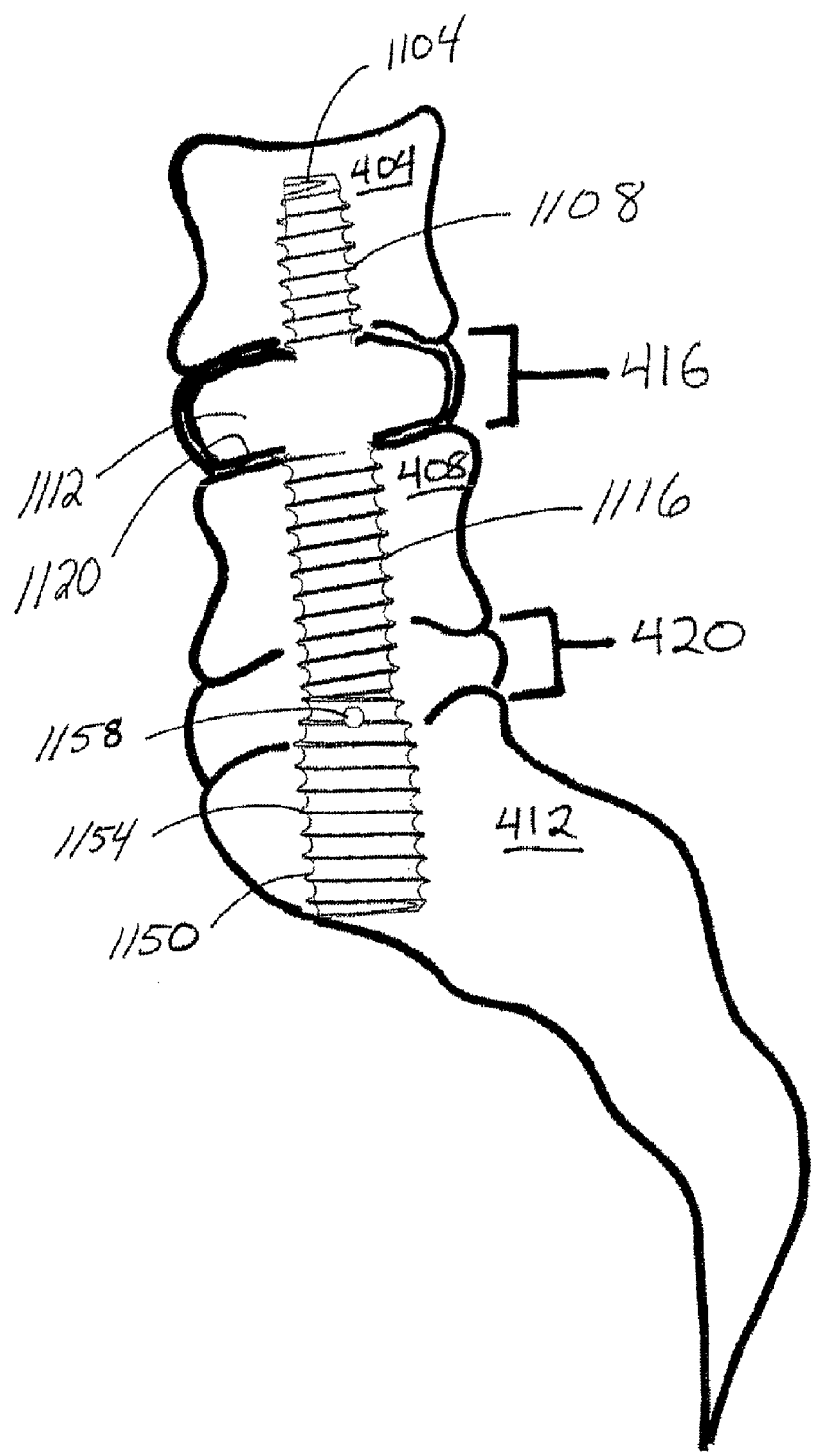
FIG. 11 shows a two-level therapy provided by the sequential installation of two axially implantable rods.

FIG. 11 shows a two-level therapy provided by the sequential installation of two axially implantable rods. Distal rod 1104 is comprised of a distal threaded section 1108, a therapeutic section 1112, and a proximal threaded section 1116. The distal threaded section 1108 and the proximal threaded section 1116 have the same thread pitch in this example and thus the insertion of the distal rod 1104 would not impose a distraction on the distal intervertebral disc space 416 as the distal rod 1104 engaged with distal vertebral body 404 and medial vertebral body 408.

Therapeutic section 1112 is shown here in outline after material has been inserted into the intervertebral space and retained by device membrane 1120. In order to make device membrane 1120 distinguishable in this drawing from the components in the motion segment, a small space has been left in the drawing between the device membrane and the other components in the motion segment. This is for purpose of illustration only as the expanded device membrane 1120 would conform to the shape of the intervertebral space. Subsequent illustrations showing analogous device membranes will likewise exaggerate the spacing between the device membrane and other components for the same reason.

The proximal rod 1150 shown in FIG. 11 has a threaded section 1154 and apertures 1158. The engagement between the distal and proximal rods is not visible in this drawing but can be done in the same manner as described above in connection with FIG. 4. Likewise the options for plugs are as described above. FIG. 11 does illustrate the point that the handedness of the threaded section 1154 does not need to be the same as the handedness of the threads used in the distal rod 1104 in order to achieve a distraction as the more proximal rod will push in the cephalad direction on the implanted more distal rod to increase the axial distance between the vertebral body engaged with the more proximal rod and the vertebral body or bodies engaged with the more distal rod.

Figure 12:
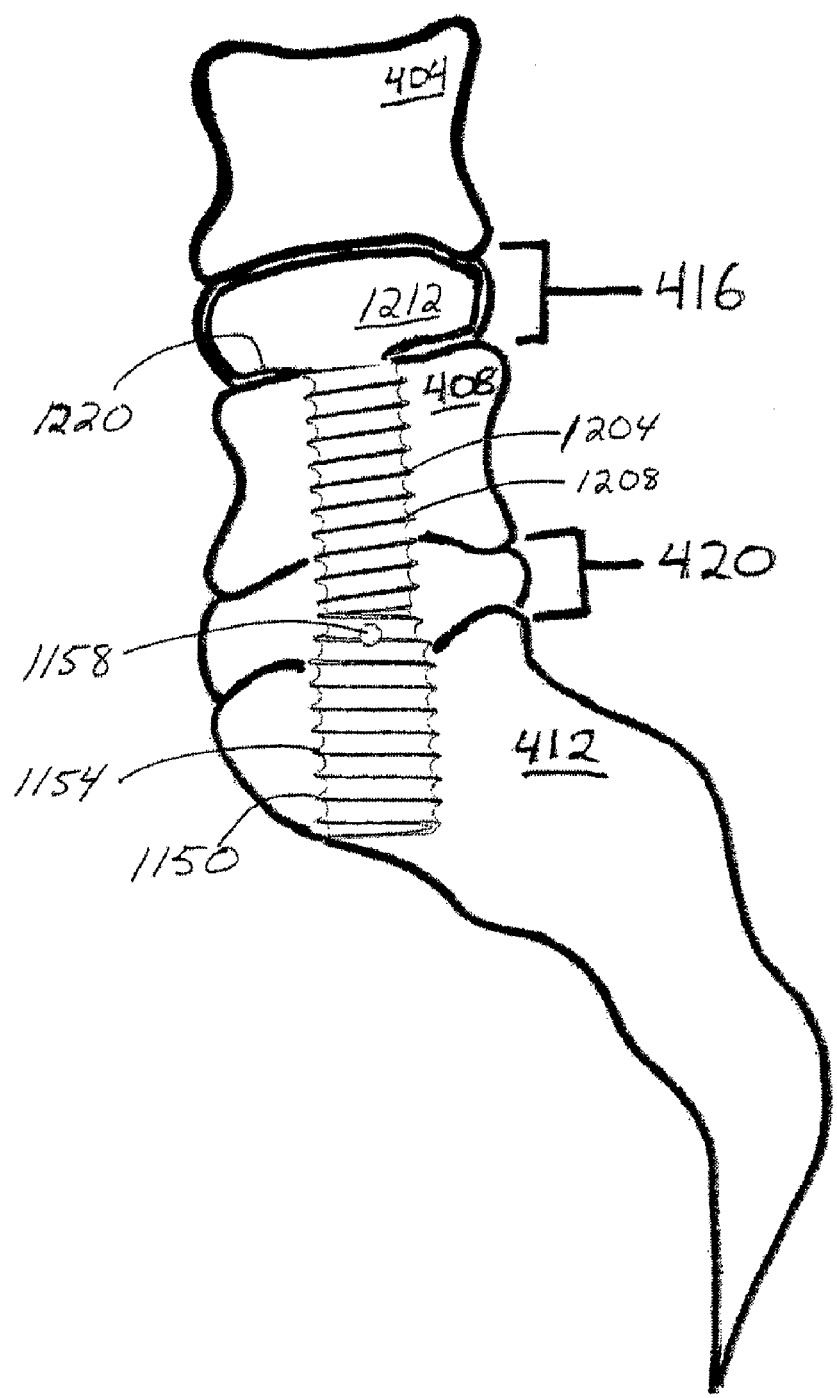
FIG. 12 shows a two-level therapy provided by the sequential installation of two axially implantable rods but does so without anchoring to the vertebral body beyond the most cephalad intervertebral disc space to receive the therapy.

FIG. 12 has a distal rod 1204 that has only one threaded section 1208. Thus the distal rod is engaged with the medial vertebral body 408 but not with the distal vertebral body 404. A therapeutic section 1212 of the distal rod 1204 extends into the distal intervertebral disc space 416. After insertion of material into expandable device membrane 1220, the device expands to a conforming fit within the intervertebral disc space 416. While this distal rod 1204 did not impose a distraction through the use of two threaded sections of dissimilar thread pitch, one of skill in the art will recognize that some distraction could be imposed hydraulically by expanding a membrane within intervertebral disc space 416. Proximal rod 1150 of FIG. 12 can be configured internally and operate as described in connection with FIG. 11.

Figure 13:
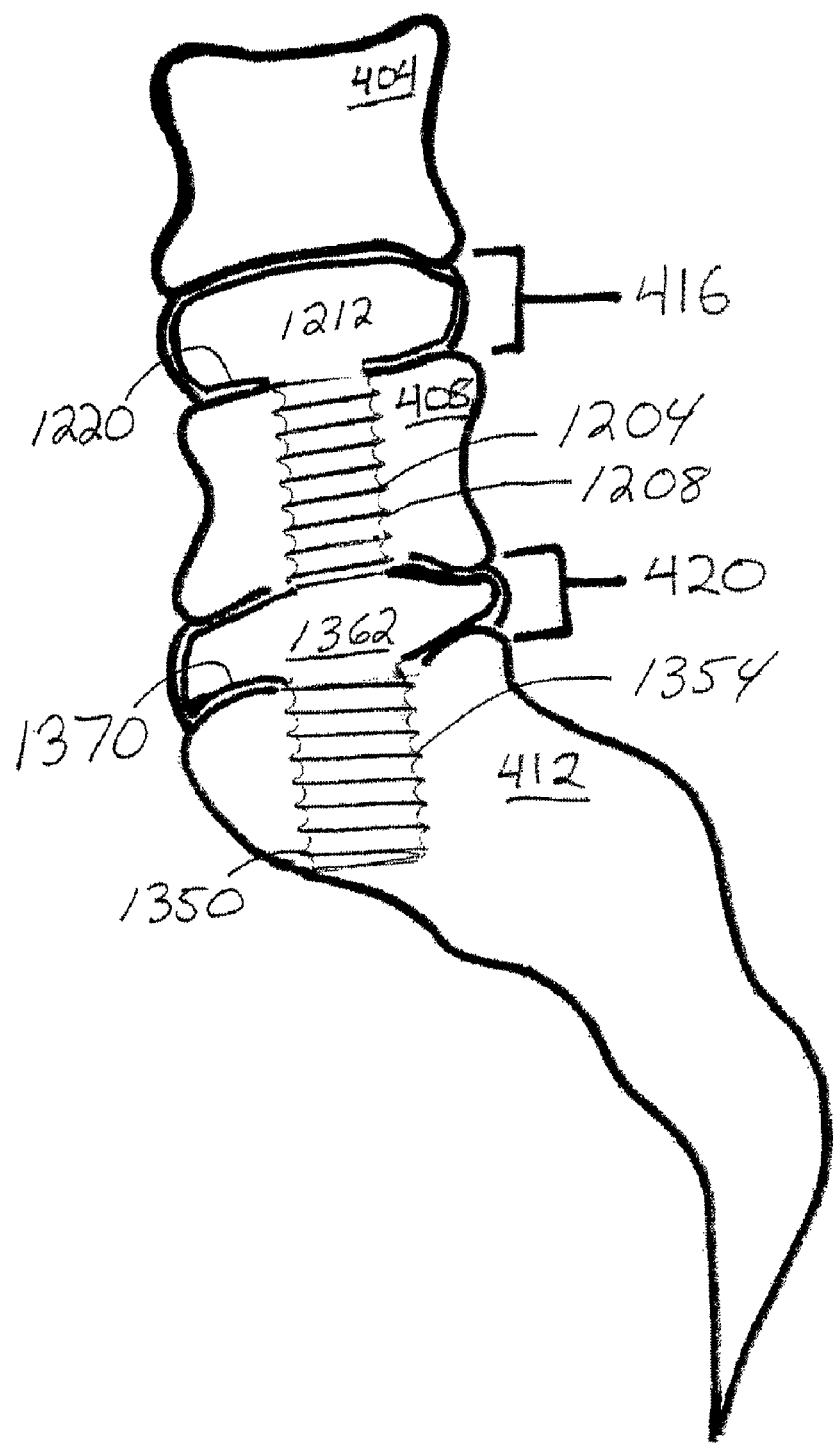
FIG. 13 shows the use of the present disclosure to provide dynamic stabilization to two adjacent motion segments.

FIG. 13 illustrates yet another use of the present disclosure to provide therapy to two adjacent spinal motion segments. More specifically, FIG. 13 shows a distal rod 1204 with the various elements described in connection with FIG. 12. FIG. 13 differs from FIG. 12 in that the proximal rod 1350 is not used to fuse the motion segment of proximal vertebral body 412, medial vertebral body 408, and proximal intervertebral disc space 420 as was done in FIGS. 11 and 12. Instead FIG. 13 shows two adjacent motion segments receiving motion management therapy to provide for post-operative mobility in both of the treated motion segments. Proximal rod 1350 would be advanced axially towards distal rod 204 by engaging the threaded section 1354 with the proximal vertebral body 412 through use of an appropriate rod driver and a rod driver engagement section in the proximal end of a longitudinal cavity in proximal rod 1350. After proximal rod 1350 engages with distal rod 1204 any subsequent rotation of proximal rod 1350 to advance the rod in the cephalad axial direction would cause the distal rod 1204 and the engaged medial vertebral body 408 to move axially away from proximal vertebral body 412. After achieving the desired level of distraction (if any) of the proximal intervertebral space, material could be provided into the proximal end of the cavity in proximal rod 1350 and out apertures in the therapeutic section 1362 of proximal rod 1350 to expand device membrane 1370.

While the preceding examples used motion management therapies that used membranes to contain the prosthetic nucleus material inserted into the intervertebral spaces through apertures in the rods, the disclosure is not limited to these particular types of motion management devices. Other motion management therapies as described in the various co-pending applications or issued patents and their priority documents can be coupled with the teachings of the present disclosure to provide therapy to two or more adjacent spinal motion segments. For example, motion management therapies that inject prosthetic nucleus material into the intervertebral space without a membrane are specifically included in the intended range of uses for the present disclosure.

TABLE A

| Multi-level Configuration | L3 | L3-L4 Disc | L4 | L4-L5 Disc | L5 | L5-S1 Disc | S1 | Figure #s |
|---|---|---|---|---|---|---|---|---|
| 3-Level | Anchor | MM + PN | Anchor | MM + PN | Anchor | MM + PN | Anchor | |
| | Anchor | MM + PN | Anchor | MM + PN | Anchor | Fusion | Anchor | |
| | Anchor | MM + PN | Anchor | Fusion | Anchor | Fusion | Anchor | Provisional FIG. 14a&b |
| | Anchor | Fusion | Anchor | Fusion | Anchor | Fusion | Anchor | 10 |
| | | PN + DD | Anchor | MM + PN | Anchor | MM + PN | Anchor | |
| | | PN | Anchor | MM + PN | Anchor | MM + PN | Anchor | |
| | | PN + DD | Anchor | MM + PN | Anchor | Fusion | Anchor | |
| | | PN | Anchor | MM + PN | Anchor | Fusion | Anchor | Provisional FIG. 10 |
| | | PN + DD | Anchor | Fusion | Anchor | Fusion | Anchor | Provisional FIG. 13 |
| | | PN | Anchor | Fusion | Anchor | Fusion | Anchor | Provisional FIG. 15 |
| 2-Level | | | Anchor | MM + PN | Anchor | MM + PN | Anchor | |
| | | | Anchor | MM + PN | Anchor | Fusion | Anchor | 11 |
| | | | Anchor | Fusion | Anchor | Fusion | Anchor | 4 could apply here but 4 is not limited to these vertebrae. |
| | | PN + DD | Anchor | MM + PN | Anchor | | | |
| | | PN | Anchor | MM + PN | Anchor | | | 13 |
| | | PN + DD | Anchor | Fusion | Anchor | | | Provisional FIG. 12 |
| | | PN | Anchor | Fusion | Anchor | | | 12 |

Table A is provided to highlight the various non-exhaustive examples of the range of applications of the teachings of the present disclosure. The table references the examples in this application and additional examples in Provisional Application No. 60/601,842 filed Aug. 14, 2004 for Method & Apparatus for Multi-Level Stabilization of the Spine which has been incorporated by reference. The various drawings referenced in the table and the text associated with those drawings in the provisional are all incorporated herein by reference. In this table anchor refers to a threaded portion of a device or rod that engages a vertebral body; PN refers to prosthetic nucleus.

Plug Driver with Retention Rod.

FIG. 14 shows a preferred driver for insertion or removal of plugs of the various types discussed above. FIG. 14A shows the driver assembly 1400. The driver assembly 1400 has a handle 1404 that is adapted for providing rotation to the driver assembly 1400 and consequently to the driven plug. The handle 1404 is connected to a driver shaft 1408 to form a driver 1412 with polygonal driver head 1416 as shown in FIG. 14B. In a preferred embodiment, the driver head 1416 is part of a removable tip 1420 that is attached to the driver shaft 1408, such as by connection pin 1424.

Retention rod 1450 is comprised of a threaded distal end 1454 and a rotation actuator 1458, in this case a knob. The retention rod 1450 can be inserted into the driver shaft 1408 and the threaded distal end 1454 extended through the driver shaft 1408 and out through the driver head 1416 as the retention rod 1450 is longer than the driver 1412. FIG. 14C shows an enlarged detail of the driver head 1416 with the protruding threaded distal end 1454.

The advantage of the driver with retention rod 1450 is that a plug can be engaged to the driver 1400 by engaging the threaded distal end 1454 with a corresponding portion of the proximal end of the plug. This can be done by holding the proximal end of the plug adjacent to the threaded distal end 1454 and rotating the rotation actuator 1458 to cause the threaded distal end to rotate relative to the driver shaft 1408 and the held plug. Once the plug is engaged with the threaded distal end 1454 and the driver head 1416, the distal end of the driver assembly 1400 can be inserted into the channel along with the engaged plug. After the distal end of the plug is inserted into the relevant device, the handle can be rotated to engage threads on the plug with threads in the device to engage the plug. After the plug is at least partially engaged with the device in the channel, the rotation actuator 1458 can be rotated to cause the threaded distal end 1454 of the retention rod 1450 to rotate relative to the driver head 1416 and the plug. Rotation in the proper direction (based on the handedness of the threads used on the threaded distal end 1454) will disengage the threaded distal end 1454 from the plug. After the plug is installed in the device, the distal end of the driver assembly 1400 can be withdrawn from the channel.

Extraction of a plug from a device would start with putting the threaded distal end 1454 of a retention rod 1450 (which is part of a driver assembly 1400) into the channel and adjacent to the proximal end of the plug to be extracted. Rotation of the rotation actuator in the appropriate direction for the threads used will cause the threaded distal end 1454 to engage with the installed plug. After the threaded distal end 1454 is engaged with the plug and the plug is engaged with the driver head 1416 then rotation of the driver assembly 1400 through the use of the handle 1404 will cause the plug to disengage from the device. After the plug is disengaged, it can be removed with the driver assembly as the driver assembly is removed from the channel because the plug is threadedly engaged with the retention rod 1450.

Properties of preferred materials for axially implantable devices are discussed at length in the U.S. Provisional Application No. 60/601,842 and the relevant material in that application, including material on pages 38-40 of that application, is incorporated herein by reference.

Alternative Embodiments

Throughout this document, there have been references to both male and female hex head fittings. Hex fittings are preferred fittings but one of ordinary skill in the art will recognize that other corresponding male and female fittings can be used to impart rotation from a driver to a driven rod, plug, or other component. With the exception of a perfect circle, almost any polygon with regular or irregular sides would work including: triangle, square, pentagon, heptagon, octagon, et cetera. Other configurations could work including shapes with curves such as crescents, ovals, semi-circles, or even an array of two or more circles that do not share the same center axis. Nothing in this specification or the claims that follow should be construed as limiting the scope of claim coverage to hexagonal drivers.

The preferred embodiment discussed in detail above uses a set of axial distraction rods so that the cross sections of the threaded sections of the rods get progressively smaller. An alternative is that two consecutive sets of threads on two different distraction rods can have the same thread and cross section. For example, if the proximal threaded section 312 of the distal distraction rod 300 and the threaded section 504 of the proximal distraction rod 500 have the same thread pattern, then keying can be useful to prevent cross threading. More specifically, it is necessary to "time" the threads so that they engage the bone at the same location, to prevent "cross-threading". Cross-threading can occur because these are "self-tapping" rods. The first set of threads of sufficient size to engage the vertebral body (rather than pass through it) will essentially tap the bore through the vertebral body. As the next threaded section reaches the previously tapped vertebral body, cross threading will occur unless the leading edge of the thread enters the track left by the first set of threads in the same place. In one aspect of the disclosure, an exchange cannula with a threaded inner diameter that docks with/attaches to the sacrum may be utilized to avoid cross-threading. Each rod can then be readily threaded through the cannula to initially engage the vertebral body at the same location. While this method can be used with an effort to perform two distractions of adjacent intervertebral spaces, it is particularly useful when performing distractions of three or more adjacent intervertebral spaces as keying eliminates the need for four progressively larger cross sections to be made in the sequence of vertebral bodies.

The preferred embodiment of the engagement section is a cylinder with a tapered leading edge (frusta-conical) such as shown by engagement section 508 in connection with FIG. 5. One of ordinary skill in the art will recognize that a pure cylinder or a cylinder with a rounded leading shoulder would be a viable solution although that shape would not tend to self-align to the same extent as the preferred embodiment. The entire engagement section could be frusta-conical (that is without a cylindrical component), however, the preferred embodiment calls for a rapid taper out to a cylinder to increase the wall thickness of the engagement section to increase the strength of this portion of the rod. Likewise, other shapes that allow for endless rotation of the more proximal rod against the more distal rod would be viable including a leading edge that resembles a hemisphere.

One of skill in the art can appreciate that provided an appropriate channel that could be created in more than four sequential vertebral bodies, that a sequence of distraction rods could include a distal distraction rod, two or more medial distraction rods, and a proximal distraction rod. Assuming that the various rods were sized appropriately for the anatomy of the sequence of motion segments, this would allow for the sequential distraction and selective application of therapy to four or more intervertebral spaces.

One of skill in the art will recognize that some of the alternative embodiments set forth above are not universally mutually exclusive and that in some cases alternative embodiments can be created that implement two or more of the variations described above.

Those skilled in the art will recognize that the methods and apparatus of the present disclosure have many applications and that the present disclosure is not limited to the specific examples given to promote understanding of the present disclosure. Moreover, the scope of the present disclosure covers the range of variations, modifications, and substitutes for the system components described herein, as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A method to axially distract a first intervertebral space between a first vertebral body and a second vertebral body, comprising the steps:
   implanting a first assembly in the first vertebral body through an access channel;
   implanting a second assembly in the second and more caudal vertebral body through the access channel; and
   using a rotating portion of the second assembly to contact a proximal end of the first assembly to push on the first assembly without rotating the first assembly to axially distract the first intervertebral space between the first vertebral body engaged with the first assembly and the second vertebral body engaged with second assembly.

2. The method of claim 1 further comprising a preliminary step of creating the access channel for use in a trans-sacral approach by boring through an anterior face of the sacrum.

3. The method of claim 2 wherein the first assembly and the second assembly are each adapted for delivery through a single access channel created during surgery with an opening at a proximal end of the access channel that receives the first assembly and the second assembly.

4. The method of claim 1 wherein the portion of the second assembly fits within an engagement zone in the proximal end of the first assembly.

5. The method of claim 1 wherein the first assembly comprises a first set of male threads for engagement with a distal vertebral body and a second set of male threads with the same handedness for engagement with a less distal vertebral body.

6. The method of claim 1 wherein the first assembly comprises a distal tip of the first assembly for placement in an intervertebral space cephalad to the first assembly and the first assembly is used to insert material into the intervertebral space cephalad to the first assembly.

7. The method of claim 1 further comprising inserting of a distal end of a plug through a lumen in the second assembly into a cavity in the first assembly before a threaded portion on the exterior of the plug is engaged with a corresponding set of threads.

8. The method of claim 7 wherein the threaded portion on the exterior of the plug engages a set of female threads in a cavity in the first assembly.

9. The method of claim 7 wherein the threaded portion on the exterior of the plug engages a set of female threads in a cavity in a first plug previously inserted into the first assembly.

10. The method of claim 1 further comprising inserting a plug in the first assembly to limit movement of material delivered to an intervertebral space through the first assembly back into the first assembly.

11. The method of claim 1 wherein the rotating portion of the second assembly contacts a thrust bearing on the proximal end of the first assembly to impart an axial force through the thrust bearing.

12. The method of claim 1 wherein implanting the first assembly in the first vertebral body includes implanting at least a portion of the first assembly in a more cephalad intervertebral space adjacent to the first vertebral body and a distal end of the first assembly is expanded to fill at least a portion of the more cephalad intervertebral space.

13. The method of claim 1 wherein implanting the first assembly in the first vertebral body includes implanting a threaded fusion rod that engages the first vertebral body and an adjacent and more cephalad additional vertebral body such that the push from the second assembly axially distracts the first intervertebral space between first vertebral body engaged with the first assembly and the second vertebral body engaged with second assembly without altering a more cephalad intervertebral space between the first vertebral body and the additional vertebral body.

14. The method of claim 13 wherein implanting the first assembly causes axial distraction of the intervertebral space between the first vertebral body and the additional vertebral body through use of dissimilar thread pitches on the first assembly.

15. The method of claim 13 further comprising the preliminary step of creating a trans-sacral axis channel with a caudal to cephalad sequence of vertebral body bores of decreasing cross sectional area for cross sections taken perpendicular to the longitudinal axis of the axis channel such that the vertebral body bores are sized relative to the major diameters of
   a first set of threads located on a distal portion of the first assembly for engagement with the additional vertebral body,
   a second set of threads on a proximal portion of the first assembly for engagement with the first vertebral body, and
   a third set of threads on the second assembly for engagement with the second vertebral body;
   allowing cephalad axial advancement of the first, second, and third set of threads of increasing major thread diameters through the axis channel without cross-threading.

16. The method of claim 13 further comprising the preliminary step of creating a trans-sacral axis channel with a caudal to cephalad sequence of vertebral body bores wherein the first vertebral body and the second vertebral body receive bores with the same cross sectional area for cross sections taken perpendicular to the longitudinal axis of the axis channel wherein the steps of:
   implanting the first assembly in the first vertebral body; and
   implanting the second assembly in the second and more caudal vertebral body are performed using a common driver and timed delivery in order to avoid cross threading.

17. The method of claim 13 wherein the additional vertebral body is a L4 vertebra, the first vertebral body is a L5 vertebra, and the second vertebral body is a sacrum.

18. The method of claim 13 wherein the additional vertebral body is a L3 vertebra, the first vertebral body is a L4 vertebra, and the second vertebral body is a L5 vertebra.

19. The method of claim 13 wherein the first assembly is used to fuse spinal therapy acts to fuse together a more cephalad motion segment comprising the additional vertebral body, the more cephalad intervertebral disc, and the first vertebral body and material is inserted into the more cephalad intervertebral space to promotes fusion, and the material travels through an interior of the first assembly.

20. The method of claim 19 further comprising fusing a first motion segment comprising the first vertebral body, the first intervertebral space, and the second vertebral body after distraction of the first motion segment including insertion of material into the first intervertebral space through the first assembly wherein the material inserted into the first intervertebral space promotes fusion.

21. The method of claim 13 wherein the first assembly is used in provision of dynamic stabilization of a more cephalad motion segment comprising the additional vertebral body, the more cephalad intervertebral disc, and the first vertebral body and material is inserted into the more cephalad intervertebral space to expand a flexible portion of the first assembly.

22. The method of claim 21 further comprising fusing a first motion segment comprising the first vertebral body, the first intervertebral space, and the second vertebral body after distraction of the first motion segment including insertion of material into the first intervertebral space through the first assembly wherein the material inserted into the first intervertebral space promotes fusion.

23. The method of claim 21 wherein the second assembly is used to in provisional of dynamic stabilization a first motion segment comprising the first vertebral body, the first intervertebral space, and the second vertebral body and material is inserted into the first intervertebral space to expand a flexible portion of the second assembly.

24. A method to selectively provide distraction to two different adjacent motion segments comprising:
   providing a selected spinal therapy to a first motion segment through use of a first assembly engaged with at least a first vertebral body;
   engaging a second assembly with a second vertebral body immediately caudal to the first vertebral body;
   pushing a proximal end of the first assembly with a rotating portion of the second assembly to push the first assembly axially away from the second vertebral body without rotating the first assembly;
   engaging a third assembly with a third vertebral body caudal to the second vertebral body; and
   pushing a proximal end of the second assembly with a rotating portion of the third assembly to push the second assembly axially away from the third vertebral body without rotating the second assembly.

25. The method of claim 24 wherein the first vertebral body is the L4 vertebra, the second vertebral body is the L5 vertebra, and the third vertebral body is the sacrum.

26. The method of claim 24 wherein a selected distraction is provided to the first motion segment through use of a threaded rod engaged with both the first vertebral body and an adjacent and more cephalad vertebral body through use of dissimilar thread pitch on threaded sections of the threaded rod.

27. The method of claim 26 wherein more cephalad vertebral body is the L3 vertebra, the first vertebral body is the L4 vertebra, the second vertebral body is the L5 vertebra, and the third vertebral body is the sacrum.

* * * * *